(12) United States Patent
Park et al.

(10) Patent No.: US 12,121,974 B2
(45) Date of Patent: Oct. 22, 2024

(54) METHOD FOR FABRICATION OF NON-SPHERICAL/ASYMMETRIC FINE PARTICLES BY USING GLASS-COATED METAL WIRES

(71) Applicant: UNIVERSITY-INDUSTRY COOPERATION GROUP OF KYUNG HEE UNIVERSITY, Gyeonggi-do (KR)

(72) Inventors: Wook Park, Gyeonggi-do (KR); Suk Heung Song, Gyeonggi-do (KR)

(73) Assignee: UNIVERSITY-INDUSTRY COOPERATION GROUP OF KYUNG HEE UNIVERSITY, Gyeonggi-do (KR)

( * ) Notice: Subject to any disclaimer, the term of this patent is extended or adjusted under 35 U.S.C. 154(b) by 1463 days.

(21) Appl. No.: 16/487,815

(22) PCT Filed: May 29, 2018

(86) PCT No.: PCT/KR2018/006062
§ 371 (c)(1),
(2) Date: Aug. 21, 2019

(87) PCT Pub. No.: WO2018/221920
PCT Pub. Date: Dec. 6, 2018

(65) Prior Publication Data
US 2020/0246866 A1    Aug. 6, 2020

(30) Foreign Application Priority Data

May 29, 2017  (KR) ........................ 10-2017-0066405
May 9, 2018   (KR) ........................ 10-2018-0053133

(51) Int. Cl.
*B22F 9/06*    (2006.01)
*B22F 1/062*   (2022.01)
(Continued)

(52) U.S. Cl.
CPC ............... *B22F 9/06* (2013.01); *B22F 1/062* (2022.01); *B22F 1/068* (2022.01); *B22F 1/08* (2022.01);
(Continued)

(58) Field of Classification Search
None
See application file for complete search history.

(56) References Cited

U.S. PATENT DOCUMENTS 5,110,334 A      5/1992  Ayers
5,240,066 A  *   8/1993  Gorynin ............... B22D 11/005
                                                     164/471
(Continued)

FOREIGN PATENT DOCUMENTS

JP    2001-310331 A   11/2001
KR   10-2010-0110352 A   10/2010

OTHER PUBLICATIONS

Mulvaney et al., Langmuir 2003 19 (11), 4784-4790 (Year: 2003).*
(Continued)

*Primary Examiner* — Lisa L Herring
(74) *Attorney, Agent, or Firm* — Quarles & Brady LLP

(57) ABSTRACT

Disclosed are: a method capable of preparing, in large-scaled quantity, nonspherical/asymmetric fine particles in which the physical factors (for example, size, shape, structure, etc.) of a fine wire (for example, glass-coated metal microwires) are controlled, through a convergence of nano technology (NT) and laser machining technology; and a use thereof applicable to various fields including bioassay and security.

21 Claims, 16 Drawing Sheets

(51) Int. Cl.
    *B22F 1/068* (2022.01)
    *B22F 1/08* (2022.01)
    *B22F 1/16* (2022.01)
    *B22F 9/04* (2006.01)
    *C03B 37/026* (2006.01)
    *C03B 37/16* (2006.01)
    *C08K 7/06* (2006.01)
    *C08K 9/02* (2006.01)
    *D01F 9/08* (2006.01)
    *D21H 17/00* (2006.01)
    *D21H 17/68* (2006.01)
    *D21H 21/42* (2006.01)
    *G01N 33/553* (2006.01)

(52) U.S. Cl.
    CPC .................. *B22F 1/16* (2022.01); *B22F 9/04* (2013.01); *C03B 37/026* (2013.01); *C03B 37/16* (2013.01); *C08K 7/06* (2013.01); *C08K 9/02* (2013.01); *D01F 9/08* (2013.01); *D21H 17/68* (2013.01); *D21H 17/73* (2013.01); *D21H 21/42* (2013.01); *G01N 33/553* (2013.01); *B22F 2009/046* (2013.01); *B22F 2302/45* (2013.01); *C08K 2201/01* (2013.01)

(56) References Cited

U.S. PATENT DOCUMENTS

| | | |
|---|---|---|
| 5,961,720 A | 10/1999 | Imaeda et al. |
| 2008/0200562 A1 | 8/2008 | Yin et al. |
| 2011/0036123 A1* | 2/2011 | Adar .................. B21C 37/042 65/45 |
| 2011/0063610 A1 | 3/2011 | Ivanov et al. |

OTHER PUBLICATIONS

Supplementary Partial European Search Report for EP 18810273.5, dated Nov. 6, 2020, 17 pages.

Donald et al., "The preparation, properties and applications of some glass-coated metal filaments prepared by the Taylor-wire process", Journal of Materials Science 31 (1996) 1139-1149.

Donald, "Production, properties and applications of microwire and related products", Journal of Materials Science 22 (1987) 2661-2679.

International Search Report for KR2018/006062, dated May 29, 2018, and its English translation, 7 pages.

* cited by examiner

Glass coated wire

METHOD FOR FABRICATION OF NON-SPHERICAL/ASYMMETRIC FINE PARTICLES BY USING GLASS-COATED METAL WIRES

TECHNICAL FIELD

The present disclosure pertains to a method for producing non-spherical/asymmetric fine particles using fine (or ultra-thin) wires. More particularly, the present disclosure pertains to a method suitable for mass production of non-spherical/asymmetric fine particles having controlled physical factors (for example, size, shape, structure, etc.) from fine wires (for example, glass-coated metal microwires) through a convergence of nano technology (NT) and laser machining technology, and a use of the same in various fields including bioassay and security.

BACKGROUND ART

Fine particles are increasingly demanded in various fields including cosmetics, printing, and optical materials, with the expectation of steady growth of the global market for functional fine particles in the future. Particularly, researches that are focusing on composite materials, medicine, bioscience, personal hygiene products, and related products have been continuously studied on their applicability.

For example, the medical application employs fine particles as a core role in drug release, molecular imaging, and so on. Thus, the importance of mass production of new functional fine particles in various fabricating or R & D fields is being reexamined all over the world.

Conventionally, spherical fine particles have been used chemically surface treatments or modifications to control their chemical properties (e.g., material, composition, etc.) depending upon application fields. In recent years, a novel functional fine particle has been highly attention with new shapes and materials as efforts are increasingly made to understand and imitate the functional roles of entities that have the various morphologies and shapes, such as DNAs, viruses, human cells, etc.

Especially, physical factors of fine particles have been reported close relationship a cell growth effect, disease diagnosis, and drug release with biological or medical applications. Also, the fabricating methods of controlled fine particles and their influences as the physical factors such as size, shape and surface have been reported.

In addition, magnetic fine particles that are widely used as molecular diagnostics in the bio/medical commercial market are based on spherical polymer particles (e.g., polystyrene, polyethylene, latex, epoxy, etc.), where sizes of the sphere are regarded as an important factor.

On the other hand, many researches have studied on technologies that can apply non-spherical/asymmetric fine particles instead of the conventional spherical fine particles. The non-spherical/asymmetric fine particles are known as a solution for overcoming the inherent properties of the spherical fine particles (for example, having significant influences on the movement and adsorption depending on particle sizes in blood vessels, digestive system, and respiratory system). Recently, non-spherical/asymmetric fine particles have rapidly used in biological, medical, pharmacological, and security areas.

Therefore, the non-spherical/asymmetric fine particles are expected to be able to overcome the technical limitations of conventional spherical fine particles because it can exhibit useful physical and chemical properties compared to spherical particles, for example, anisotropic distribution, easy local surface modification, and compartmentalization.

However, in order to produce the fine particles having a non-spherical/asymmetric structure, it is necessary to modify the conventional fine particles manufacturing method or to create a new manufacturing method.

As approaches for directly obtaining non-spherical/asymmetric fine particles, optofluidic technique with lithography (specifically, hydrogel fine particles product in fluidic channels using lithographic systems), printing soft lithography (specifically, polymer fine particles product through replication using the pattern frame, where PFPE molds with low wettability are used instead of PDMS molds), micro-molding (controlling the surface tension of polymer in a pattern frame in order to fabricate 3D particles such as convex or concave shapes), or a combination thereof have been developed.

Furthermore, as approaches for indirectly obtaining non-spherical/asymmetric fine particles, stretching-induced deformation of spherical fine particles (particles are liquefied using heat or toluene, then stretched in a uni- or bidirectional orientation, followed by cooling or toluene extraction. The other method is that the fine particles are stretched under air in order to form pores, followed by liquidized or solidified by use of heat or toluene). These shapes are ribbons with curled ends, bicones, diamond disks, emarginate disks, flat pills, elongated hexagonal disks, ravioli, and tacos types of micropaticles. Others selective extraction are proposed for indirectly fabrication.

Most of the above prior art techniques are based on chemical reactions. These techniques involve complicated steps in the production of fine particles or produce in small quantities. Therefore, there are limitations in mass production for commercialization.

Now, there is highly need for a new method for manufacturing a large-scale production of non-spherical/asymmetric fine particles in an easy way.

DETAILED DESCRIPTION OF THE INVENTION

Technical Problem

Accordingly, an embodiment of the present disclosure provides a method for producing non-spherical/asymmetric fine particles in a large-scale production and in a more convenient manner compared to conventional techniques.

Another embodiment of the present disclosure provides a method for producing non-spherical/asymmetric fine particles suitable for use in bioassay with large-scale production and security materials (or indentification) with encoded information.

Technical Solution

A first aspect of the present disclosure provides a method for production of non-spherical/asymmetric fine particles, the method comprising the steps of:
 filling a glass tube with a metal;
 drawing the metal-filled glass tube while melting a lower portion of the glass tube by heating;
 cooling the drawn melt to form glass-coated metal microwires;
 positioning at least one of the glass-coated metal microwires in a plurality of grooves arranged in a width direction on a wire holder; and cutting the at least one of the glass-coated metal microwires positioned on the wire holder, in a traverse direction at predetermine distances in a non-contact machining process using a laser having a pulse width shorter than the heat propagation time of the glass-coated metal microwires.

Provided according to a second aspect of the present disclosure is a method for production of non-spherical/asymmetric fine particles, the method comprising the steps of:
  melting a metal by heating while separately heating a glass material to a temperature at which the glass material is drawable;
  drawing the heated glass material while loading the melted metal to the inside of the glass material;
  cooling the melted metal-loaded, drawn glass material to form glass-coated metal microwires;
  positioning at least one of the glass-coated metal microwires in a plurality of grooves arranged in a width direction on a wire holder; and
  cutting the at least one of the glass-coated metal microwires positioned on the wire holder, in a traverse direction at predetermine distances in a non-contact machining process using a laser having a pulse width shorter than the heat propagation time of the glass-coated metal microwires.

Provided according to a third aspect of the present disclosure is a method for production of non-spherical/asymmetric fine particles, the method comprising the steps of:
  dispersing metal powder in an ultraviolet light-curable compound to prepare a flowable metal dispersion and separately, drawing a glass tube into a glass wire while heating the glass tube;
  loading the flowable metal dispersion into the drawn glass wire;
  exposing the flowable metal dispersion-loaded, drawn glass wire to ultraviolet light to cure the ultraviolet-curable compound in the flowable metal dispersion, thus forming glass-coated metal microwires;
  positioning at least one of the glass-coated metal microwires in a plurality of grooves arranged in a width direction on a wire holder; and
  cutting the at least one of the glass-coated metal microwires positioned on the wire holder, in a traverse direction at predetermine distance gaps in a non-contact machining process using a laser having a pulse width shorter than the heat propagation time of the glass-coated metal microwires.

According to a fourth aspect of the present disclosure, binders for detection of diagnostic reagents may be coated on the non-spherical/asymmetric fine particles produced by the above-mentioned methods.

According to a fifth aspect of the present disclosure, cryptic codes may be planted on the non-spherical/asymmetric fine particles produced by the above-mentioned methods.

Advantageous Effects

A method for producing non-spherical/asymmetric fine particles, provided according to an embodiment of the present disclosure, can effectively pass the barriers that the conventional techniques have encountered in commercialization. The method is economically advantageous because it is based particularly on the manufacture of fine wires and thus can produce non-spherical/asymmetric fine particles in large-scaled quantity within a short time. Furthermore, the non-spherical/asymmetric fine particles produced according to each embodiment of the present disclosure can find wide the bioassay wherein non-applications in the spherical/asymmetric fine particles are used as a binding matrix for detection of various targets are immobilized, and in the security (identification) area wherein cryptic codes are introduced into the fine particles.

Figure 10A:
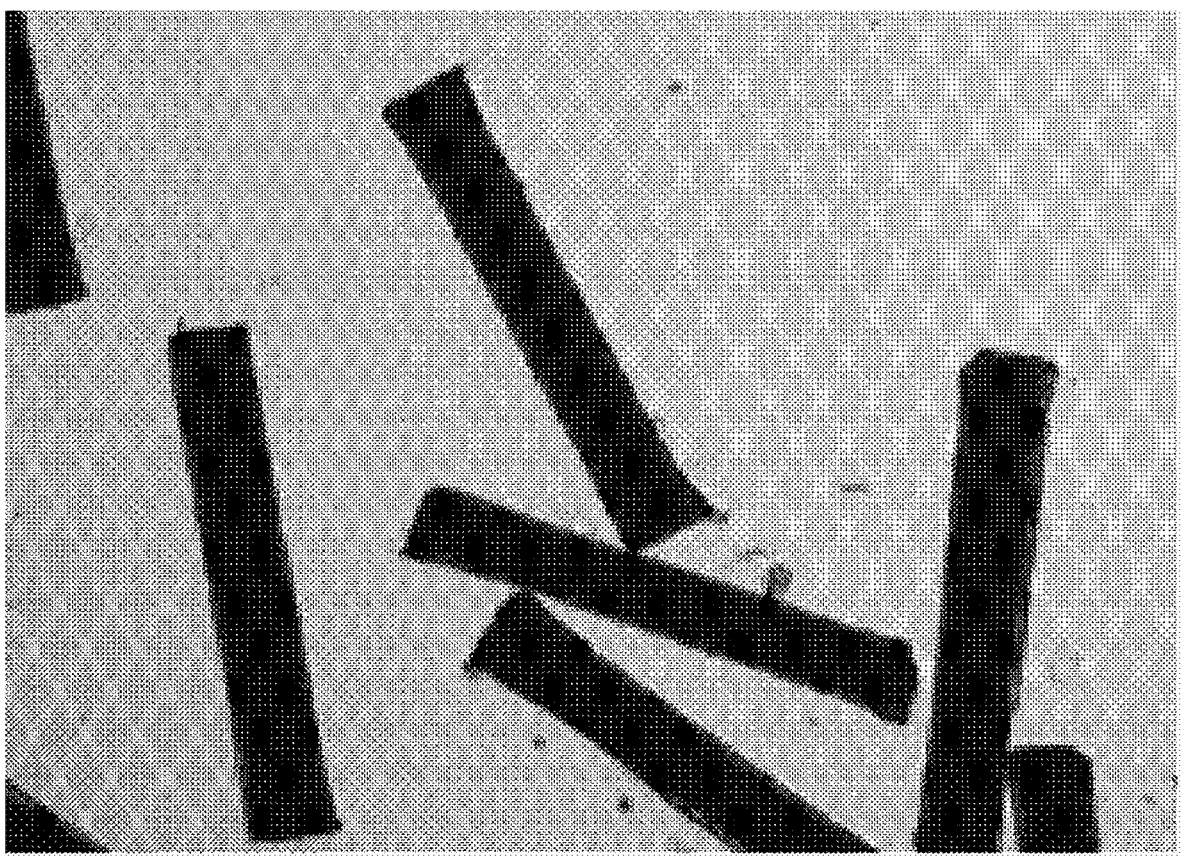
FIGS. 10A and 10B, respectively, are a bright field microscope and a red fluorescence microscope image (filter band: 575 nm) of non-spherical/asymmetric fine particles the surface of which has been subjected to an antigen-antibody reaction using mouse serum (primary antibody)
Figure 10B:
Figure 10C:
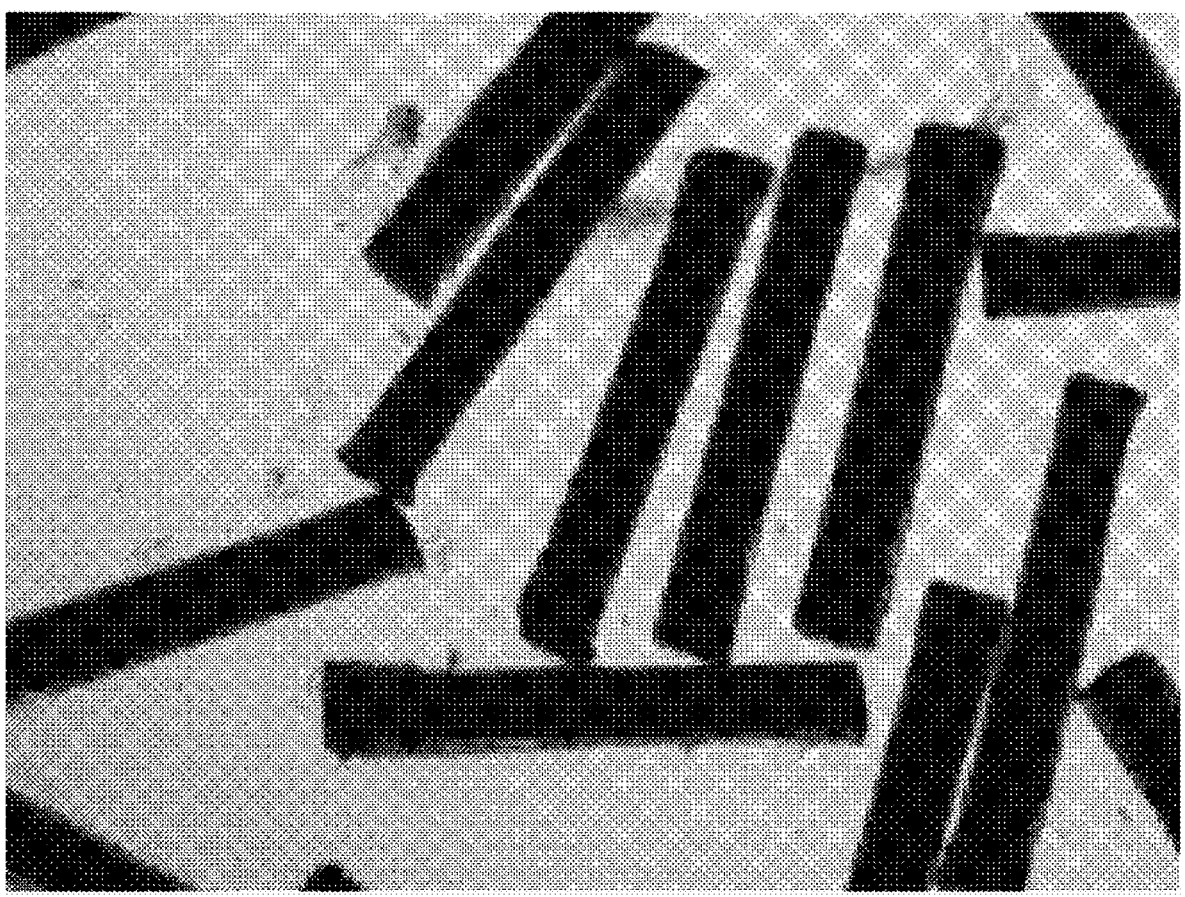
Figure 10D:
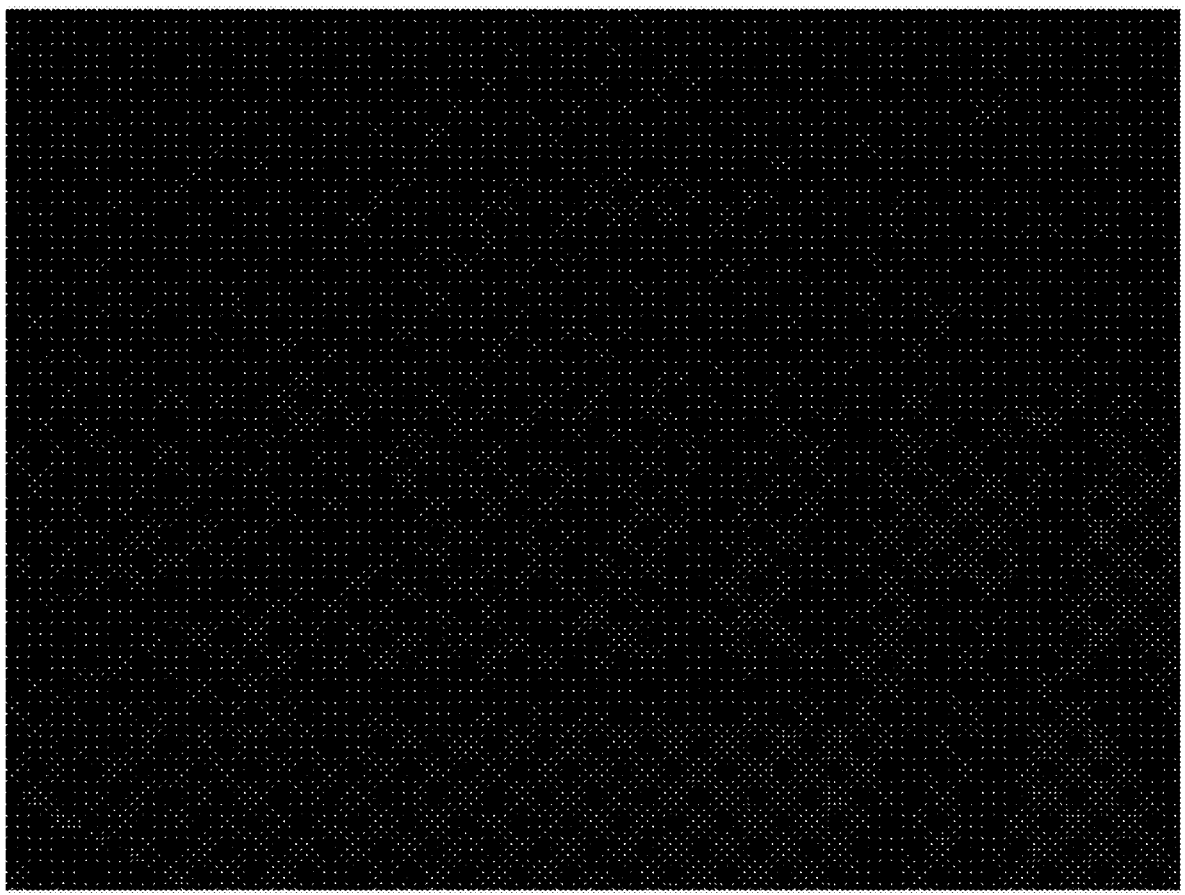
Figure 11:
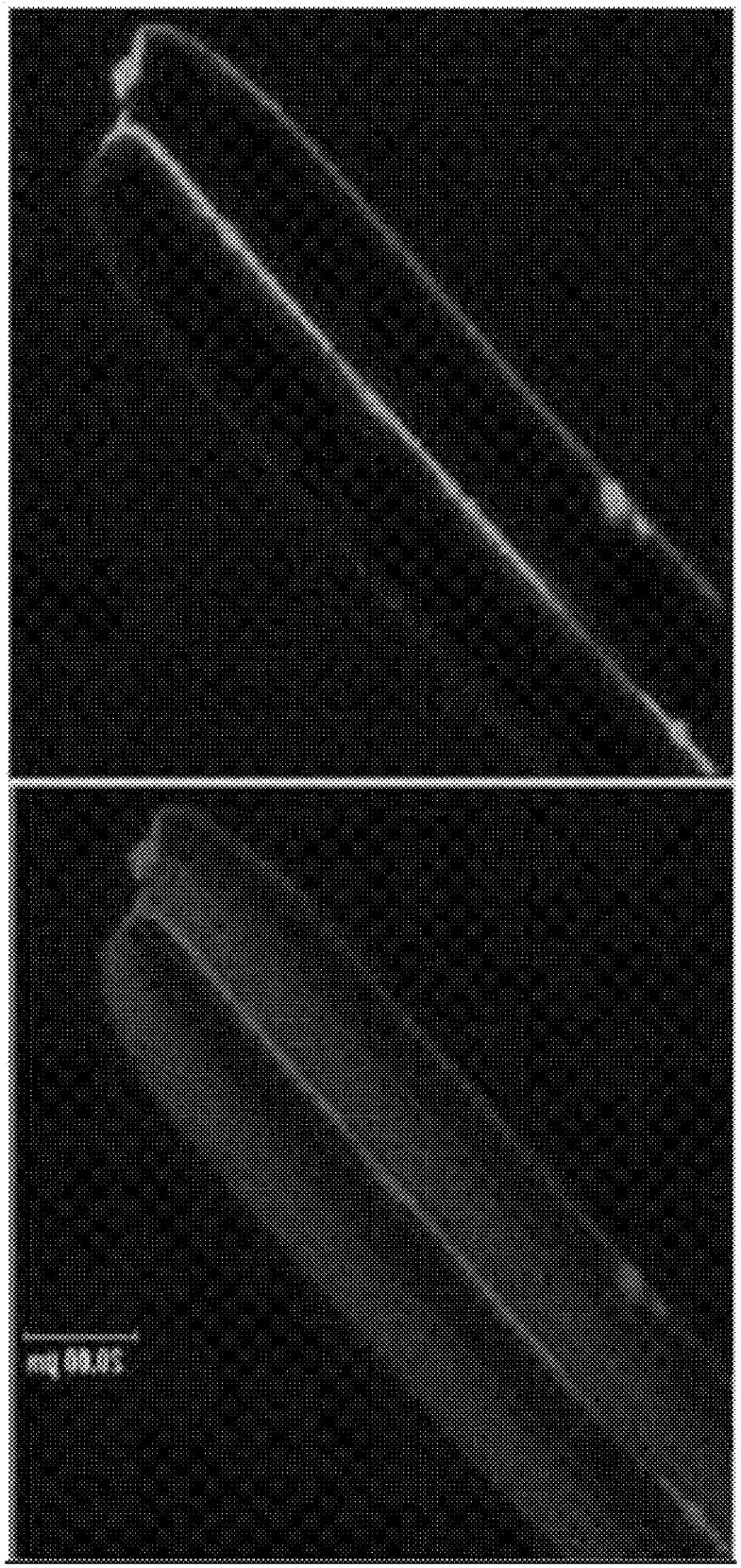
Figure 12:
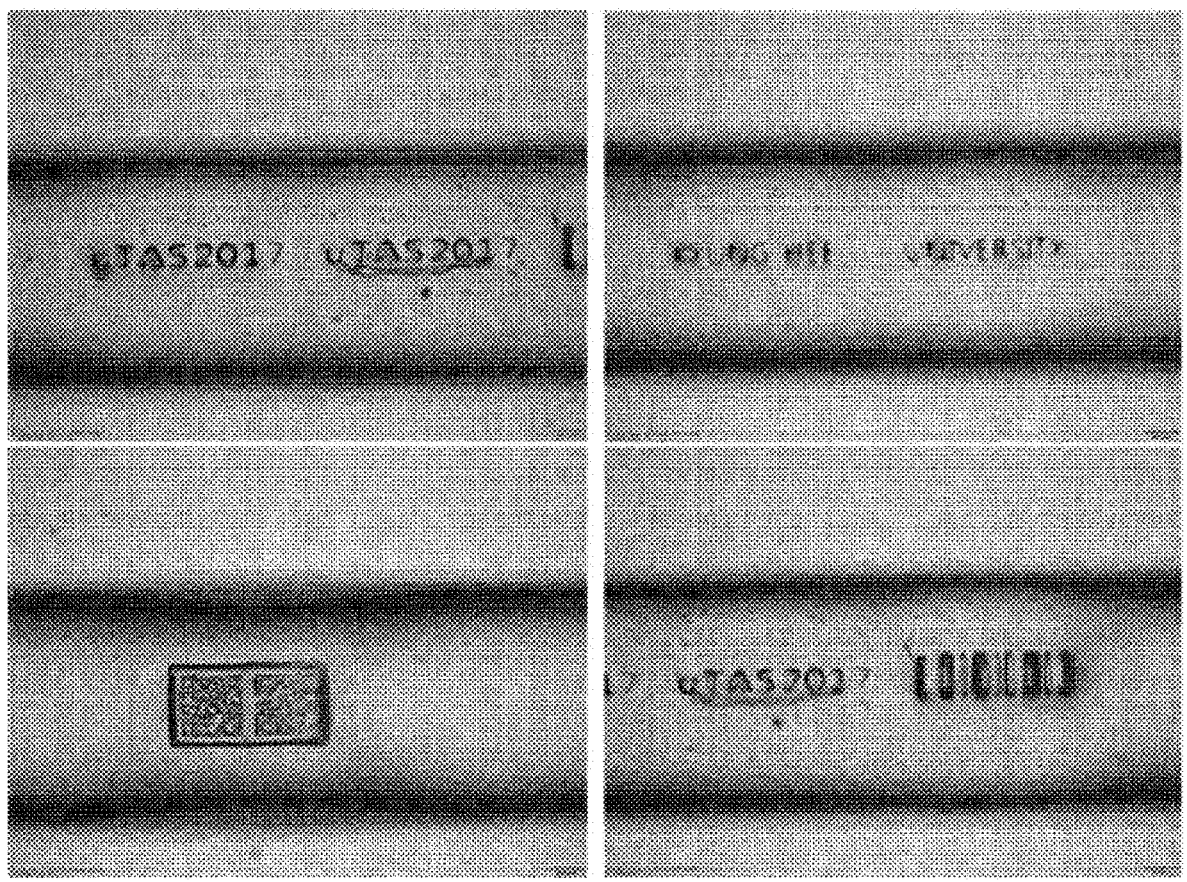

and goat anti-mouse IgG-biotin (secondary antibody), followed by fluorescent immunostaining with biotin and (phycoerythrin), PE-streptavidin-fluorescent body (PE eFluore 610, alexa 568);

FIGS. 10C and 10D, respectively, are a bright field microscope image and a red fluorescence microscope image (filter band: 575 nm) of non-spherical/asymmetric fine particles the surface of which has been subjected to non-immunoreaction with mouse serum (primary antibody) and goat anti-mouse IgG-biotin (secondary antibody);

FIG. 11 is a fluorescence microscope image (40-fold magnification) illustrating the diagnosis (or detection) using two fluorescent materials (amin-FITC, green and red) bound to the surface of the surface-modified non-spherical/asymmetric fine particles; and FIG. 12 shows optical microscope images (10-fold magnification) of surfaces of variously impressed (letters and symbols) and coded (encoded) non-spherical/asymmetric fine particles.

BEST MODE FOR CARRYING OUT THE INVENTION

The present disclosure may be fully achieved through the following description. It should be understood that the following description gives preferred embodiments of the present invention, and the present invention is not necessarily limited thereto. Further, for the sake of description, the appended drawings are exaggeratingly depicted relative to the thicknesses or heights of actual parts or ratios with other parts, which may be appropriately understood in accordance with the specific intention of the related description which will be described later.

The documents mentioned above may be understood to be incorporated herein by reference. Terms used herein may be defined as follows.

"Glass" is understood to refer to fused products of inorganic substances cooled to a solid phase without a crystallization process or a vitreous material formed by a chemical means such as a sol-gel process or by a soot process.

"Metal" may be understood to mean a metal alloy as well as a single metal.

"Drawing" may apprehensively mean a process in which a material is elongated using tension or under a load to permanently reduce the cross section thereof.

"Dispersion" or "dispersed substance" may mean the inclusion of ingredients or structures (dispersoids) of different phases in a fluid medium (dispersion medium), wherein the dispersoids may be uniformly or non-uniformly dispersed.

"Fine wire" may exist as a single member or multiple members and may also mean a fiber comprising at least one metal material.

"Glass-coated metal microwires" is a composite material composed of metallic glass or amorphous metal having a glass coat thereon and may comprise a metal core coated with a glass coating layer as thin as a micro level and having a micro-level diameter.

"Nanocrystalline metal" is metal in which a crystalline phase exists and may mean a metal or metal body in which grains have a number average size of less than 1 μm, particularly about 10 to 100 nm, or about 1 to 10 nm.

"Paramagnetism" is a form of magnetism whereby certain materials form magnets even in the absence of an external magnetic field.

"Superparamagnetic material" may mean a certain material that exhibits strong magnetism only in the presence of a magnetic field.

"Rubber magnet" may mean a soft magnet made from a mixture in which magnetic powder (e.g., ferrite powder) is incorporated into a rubber and/or plastic matrix.

"Biological substance" may mean any substance that may have an influence on physical or biochemical characteristics of a biological organism and may be intended to encompass any organic and/or inorganic ingredient derived from microbiological organisms, such as biological organic materials including various carbohydrates, amino acids, proteins, etc.; water; and biological inorganic ingredients including inorganic salts. Further, "biological substance" may be understood inclusive of various drugs that may have a medical and/or physiological influence on biological organisms.

"Immobilization" may mean the attachment of a certain material to a substrate via a covalent bond or a non-covalent bond in a direct or indirect manner.

Throughout the specification, unless explicitly described to the contrary, the word "comprise" and variations such as "comprises" or "comprising" will be understood to imply the inclusion of stated elements but not the exclusion of any other elements.

Furthermore, throughout the description, the terms "on" and "over" are used to refer to the relative positioning, and mean not only that one component or layer is directly disposed on another component or layer but also that one component or layer is indirectly disposed on another component or layer with a further component or layer being interposed therebetween. Also, spatially relative terms, such as "below", "beneath", "lower", and "between", may be used herein for ease of description to refer to the relative positioning.

Manufacture of Glass-Coated Metal Microwires

According to the present disclosure, the glass-coated metal microwires can be manufactured largely in three exemplary methods as described in great detail below.

A. First Method

A method for preparation of non-spherical/asymmetric fine particles according to one embodiment of the present disclosure comprises filling a glass tube with metal and drawing the glass tube under a heating condition to manufacture the glass-coated metal microwires. This method is based on the Talyor-Ulitovsky technique the principle of which is disclosed in, for example, WO1993/005904 A2. This patent document is incorporated herein by reference.

Figure 1A:
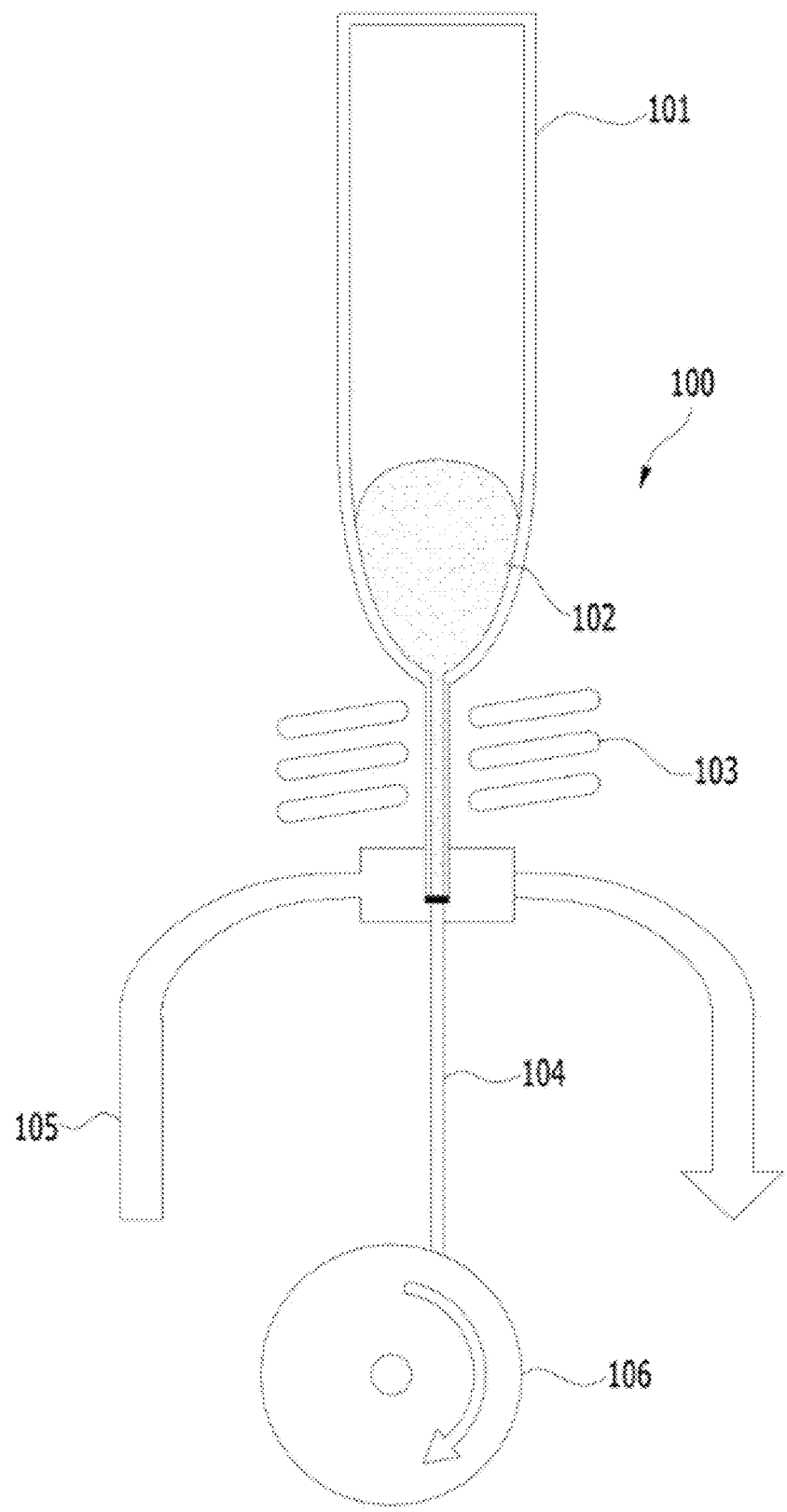
FIG. 1A is a schematic view illustrating an embodiment of a first method for manufacture of glass-coated metal microwires.

FIG. 1 depicts an embodiment of a first method for manufacture of glass-coated metal microwires.

In the system 100 for manufacture of the glass-coated metal microwires, a glass tube 101 is filled (charged) with metal 102 and positioned on a heating zone equipped with a heating means 103. For example, the glass tube 101 has an inner diameter of about 0.2 to 2 mm, particularly about 0.3 to 1.5 mm, and more particularly about 0.5 to 1 mm.

The heating means 103, as shown, may be arranged at a lower portion of the glass tube 101 or at a position adjacent thereto. The metal 102 to be loaded into the glass tube may be, for example, a solid-phase material particularly in the form of powder. In this regard, the metal powder may range in size (diameter), for example, from about 40 to 300 μm, particularly from about 50 to 200 μm, and more particularly from about 70 to 150 μm.

However, so long it is loaded into the glass tube 101, the metal 102 may be in various forms such as lumps, beads, ingots, rods, and the like, without limitation to a powder form only.

The metal loaded into the glass tube 101 is heated to the melting point thereof to form droplets. While the loaded metal 102 is melted in the heating zone, a portion of the glass tube 101 adjacent to the molted metal becomes softened to surround the metal droplets. In detail, while the loaded metal 102 is melted, the glass that is substantially higher in melting point than the metal is heated by the heat transferred from the heating means 103 to a temperature at which drawing can be performed, particularly to the softening point thereof.

According an exemplary embodiment, the heating means 103 may be an induction heating device known in the art and particularly may be an inductor. For example, because an inductor has a spiral coil (e.g., copper material) wound therein, the inside of the coil may form the heating zone. The number may be chosen in consideration of the desired height of the melted metal. As such, the heating zone is heated by eddy-current loss formed at a required frequency by the magnetic field. In addition, the heating means 103 may be a high-frequency inductor. In this regard, the frequency may range from about 0.5 to 800 kHz and particularly from about 10 to 500 kHz, and these range should be understood for exemplary purposes.

Within the heating zone, the temperature may be maintained at, for example, about 200 to 2,000° C., particularly about 400 to 1,500° C., and more particularly about 600 to 1200° C., but may be changed depending on kinds of the core metal, materials of the glass tube, etc.

As for the glass tube 101, its material may be, for example, soda lime; borosilicate; aluminosilicate; silica; alkali silicate; Pyrex®; quartz; or glass containing, as main ingredient, lead oxide, tellurium dioxide or silica, and its softening point may range typically from about 1,000 to 1,900° C. and more typically from about 1,100 to 1,700° C.

The metal loaded into the glass tube 101 may be, for example, (i) a magnetic metal or an alloy thereof, (ii) a magnetic metal or an alloy thereof plus copper (Cu), gold (Au), silver (Ag), iron (Fe), platinum (Pt), or a combination thereof, or (iii) copper (Cu), gold (Au), silver (Ag), iron (Fe), platinum (Pt), or a combination thereof. According to an exemplary embodiment, the metal may be superparamagnetic.

An exemplary melting point of the core metal that can be loaded into the glass tube 101 may range typically from about 800 to 1,700° C. and more typically from about 900 to 1,500° C., but may change according to kinds of the metal, metal proportions in the alloy, etc. In a certain embodiment, the difference between the softening point of the glass tube 101 and the melting point of the core metal may be, for example, about 200 to 800° C. and particularly by about 150 to 500° C.

By way of example, the magnetic metal may be represented by the following General Formula 1:

  [General Formula 1]

wherein, TL is transition metal selected from the group consisting of Fe, Co, Ni and a combination thereof, TE is selected from the group consisting of Cr, Mo, Nb and a combination thereof, R is rare-earth metal selected from the group consisting of Gd, Tb, Sm and a combination thereof, M is selected from the group consisting of B, Si, C and a combination thereof, and x is 0.5 to 0.95 (particularly 0.6 to 0.9, and more particularly 0.65 to 0.85).

In this regard, cobalt alloys or iron-rich alloys are representative of magnetic metal. In a certain embodiment, copper may be added to or incorporated in a small amount (for example, up to about 5 atom % and particularly up to about 3 atom %) into a magnetic metal to increase the number of nucleation centers and to promote nano-crystallization.

Next, the molten material of the metal in the glass tube 101, which accounts for the core of the glass-coated fine wire, enters and fills in the glass capillary while being is drawn. In an exemplary embodiment, the atmosphere of inert gas (for example, an argon gas) may be provided inside the glass tube 101 during the drawing process. Through the drawing process, a fine wire 104 in which the metal core is completely coated with glass can be obtained. The amount of the glass used in the above process is balanced with the continuous supply of the glass tube 101 passing through the heating zone. The drawn fine wire 104 is solidified while being cooled by a cooling means 105 arranged at the rear of heating means 103.

According to one embodiment, the cooling means 105 may spray (in detail, jet spray) a coolant to the surface of the fine wire (capillary) in a direction traversing across the drawing direction. In this case, at least part of the drawn fine wire 104 is immersed in the coolant. Meanwhile, the cooling rate of the fine wire by the coolant can be determined in consideration of the diameter of the fine wire (for example, the cooling rate may be increased for a large diameter of the fine wire). As such, when the cooling rate of the drawn fine wire 104 is appropriately controlled, the core metal within the glass-coated metal microwires may exhibit crystallinity, particularly nano-crystallinity.

According to an exemplary embodiment, the coolant may be water, oil, or various refrigerants and particularly water. When used as a coolant, water is easier to control the cooling rate than other refrigerants (for example oil) and may not cause the phenomenon of degradation or oxidation of the glass coat (shell). In another embodiment, salt-containing water may be used as a refrigerant and may increase the cooling rate, compared to water. In this case, examples of the salt contained in the coolant include sodium chloride, potassium chloride, and a combination thereof.

According to another embodiment, slow cooling by air and fast cooling by water may be combined in a stepwise manner. In detail, partial crystallization is induced by slow cooling, followed by fast cooling to stop the excessive growth of grains. In this regard, the heating means 103 and the cooling means 105 may be distant from each other by about 10 to 80 mm, particularly about 20 to 60 mm, and more particularly about 30 to 50 mm. In this regard, the cooling distance is a factor that influences the magnetic property (coercive force, that is, the opposing magnetic intensity that must be applied to a magnetized material to remove the residual magnetism) and may be varied according to kinds of the magnetic metal, metal proportions in the alloy, etc.

According to an exemplary embodiment, the drawing speed of the fine wire may range, for example, from about 10 to 800 m/s, particularly from about 50 to 300 m/s, and more particularly from about 70 to 200 m/s. Too high or low a drawing speed may cause twisting or cutting of the wire. Thus, the drawing speed may be preferably adjusted within the above range in consideration of diameters of the fine wire, etc. For example, when a small diameter of the fine wire is desired, a relatively high drawing speed is needed while a relatively low drawing speed may be set for a large diameter of the fine wire.

As described above, the solidified fine wire 104 is recovered by a winding device 106 installed in the system. According to an exemplary embodiment, the winding device may be in a coil form and particularly may be a wire bobbin.

According to an exemplary embodiment, the core metal of the glass-coated metal microwires may have a diameter of, for example, about 30 to 100 μm, particularly about 40 to 80 μm, and more particularly about 50 to 70 μm. In addition, the glass coat (shell) may range in thickness from, for example, about 10 to 100 μm, particularly about 30 to 80 μm, and more particularly about 40 to 70 μm. In addition, the fine wire may have a total diameter of, for example, about 50 to 200 μm, particularly about 60 to 150 μm, and more particularly about 70 to 100 μm.

The glass-coated metal microwires 104 thus manufactured may be typically wound around a winding device 106 in a continuous manner to a length of about 1 to 15 km, and more typically to a length of about 5 to 10 km and may be packaged in a wound form. As will be described later, the glass-coated metal microwires may be used to prepare non-spherical/asymmetric fine particles.

Figure 1B:
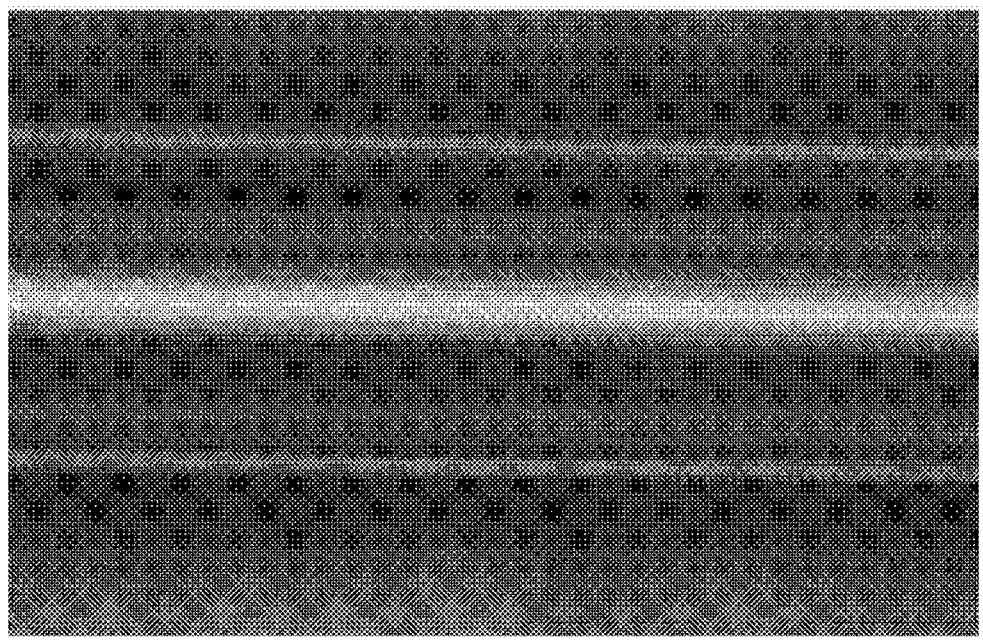
FIG. 1B is an optical microscope image showing the appearance of the glass-coated metal microwires practically manufactured according to an embodiment of the first method and wound around a wire bobbin.

FIG. 1B shows the appearance of the glass-coated metal microwires (cobalt-based metal core coated with glass) practically manufactured according to the first method and wound around a wire bobbin. According to the drawing, the glass-coated metal microwires has a total diameter of about 80 μm.

B. Second Method

In an embodiment of the present disclosure, the method for manufacture of the glass-coated metal microwires comprises separately melting metal, and drawing a glass material while loading or injecting the molten metal into the glass material.

In detail, a system for manufacture of the glass-coated metal microwires largely comprises a metal melting region, a glass-coating region, and a cooling region. The principle of this method is disclosed in U.S. Patent Publication No. 20110036123 A1, which is incorporated herein by reference. However, this patent document, which focuses upon the fabrication of glass-coated cables, differs from the production techniques of non-spherical/asymmetric fine particles by use of the glass-coated metal microwires, as will be described later, in terms of specific applications.

Figure 2A:
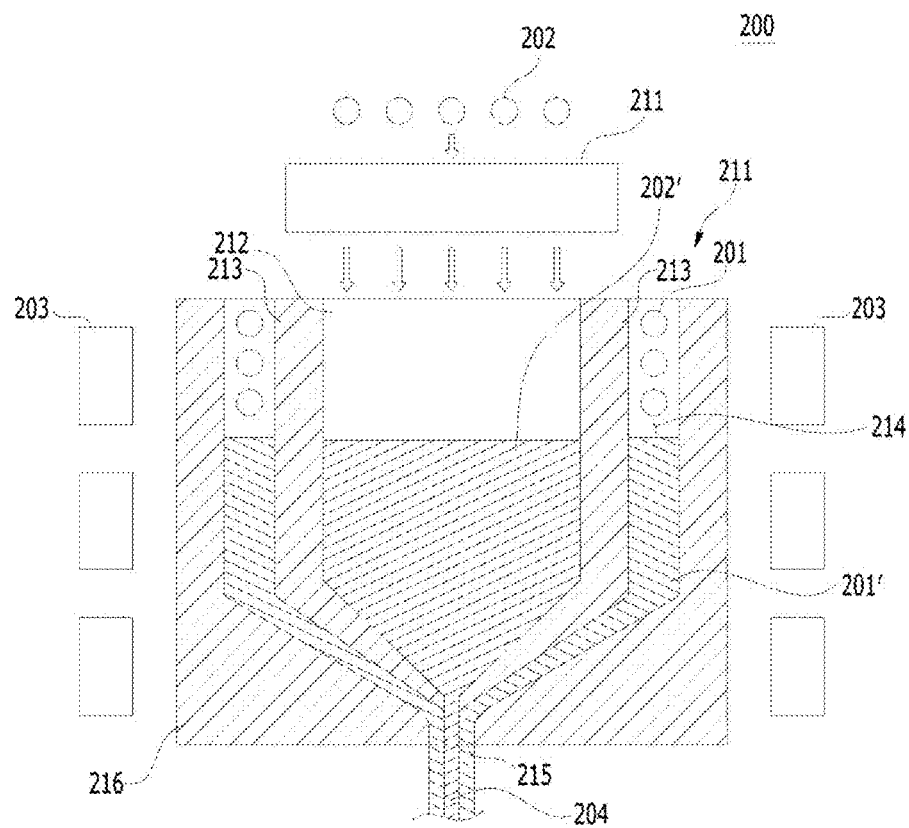
FIG. 2A is a schematic view illustrating an embodiment of a second method for manufacture of glass-coated metal microwires.

FIG. 2A is a schematic diagram illustrating the second method for manufacture of the glass-coated metal microwires. Hereinafter, descriptions overlapping with those of the first method are omitted.

In the depicted manufacturing system 200 for the glass-coated metal microwires, a metal 202 in a solid phase is introduced into a metal melting device 211 separately installed in the system and heated to at least the melting point thereof. So long as the metal melting device 211 can melt metal by generating heat so that the metal is allowed to be loaded into the cavity of a glass that is in a drawable state at the rear thereof, any heating means known in the art may be used without any particular limitation. The metal melting device 211 may refer to, for example, a crucible, a furnace, an oven, etc. such heating may be performed using, for example electromagnetic induction, microwave, etc.

In addition, the metal melting device 211 preferably supplies or transfers molten metal to the glass coating region as possible as incessantly so as to allow the continuous production of the glass-coated microwire. According to circumstances, even though molten metal is transferred to a molten metal supply space 212 in a non-continuous manner, the metal device can be applied as long as the molten metal is continuously loaded to the inside of the glass that is being drawn. Metal 202 may have any shape and dimensions and, for example, may be in the form of a lump, a bead, an ingot, etc.

As such, the molten metal is transferred through the upper opening of the glass coating device 211 into the molten metal supply space 212 in the glass coating device. In the illustrated embodiment, the funnel-type molten metal supply space 212 in glass coating device is located at the central region and configured to allow the molten metal to be transferred through a tapered lower outlet 215.

Also provided is a glass supply space 214, which has a funnel shape as in the molten metal supply space 212, in a substantially concentric arrangement so as to surround the outside of the molten metal supply space 212, and is separated from the molten metal supply space 212 by a first partition 213. The glass supply space 214 is defined by the first partition 213 and a second partition 216 and has an upper opening for introducing a glass material therethrough.

In an exemplary embodiment, the first partition 213 and the second partition 216 should continuously maintain the molten state of the metal and heat the glass to a drawable level by using the heat energy transferred from a heating means 203 (e.g., an inductor, a heating block, etc. described above) provided outside the glass coating device in addition to serving to define the respective boundaries of the molten metal supply space 212 and the glass supply space 214. Therefore, the first partition 213 and the second partition 216 advantageously exhibit thermal conductivity as well as the mechanical properties of continuously sustaining the molten metal supply space 212 and the glass supply space 214 and thus may be made of iron or iron alloy, stainless steel, etc.

Meanwhile, the glass material 201 introduced into the glass supply space 214 is not morphologically limited in particular and may have a shape of, for example, glass powder, glass balls, glass tubes, etc, as described above. The glass material 201 introduced into the glass supply space 214 is heated by a heating means to a drawable state, for example, at least a softening point (softened state). As such, the drawable glass 201' is moved to the lower outlet 215, drawn under tension while forming a capillary, and combined with the molten metal in such a manner that the glass surrounds the molten metal discharged together through the lower outlet 215. In addition, the molten metal must be discharged continuously. As a result, the glass-coated metal microwires (204) in which a glass coat (shell) is formed on the metal core can be formed.

Even though explicitly depicted in FIG. 2A, the manufacturing system 200 of f the glass-coated metal microwires may comprise a winding device (not shown) for drawing the combination of glass/metal while applying tension thereto. In addition, the drawn glass-coated metal microwire 204 may be cooled by a cooling means, for example, a refrigerant, in such a jet spraying manner. The molten metal within the glass shell can be solidified by cooling.

Figure 2B:
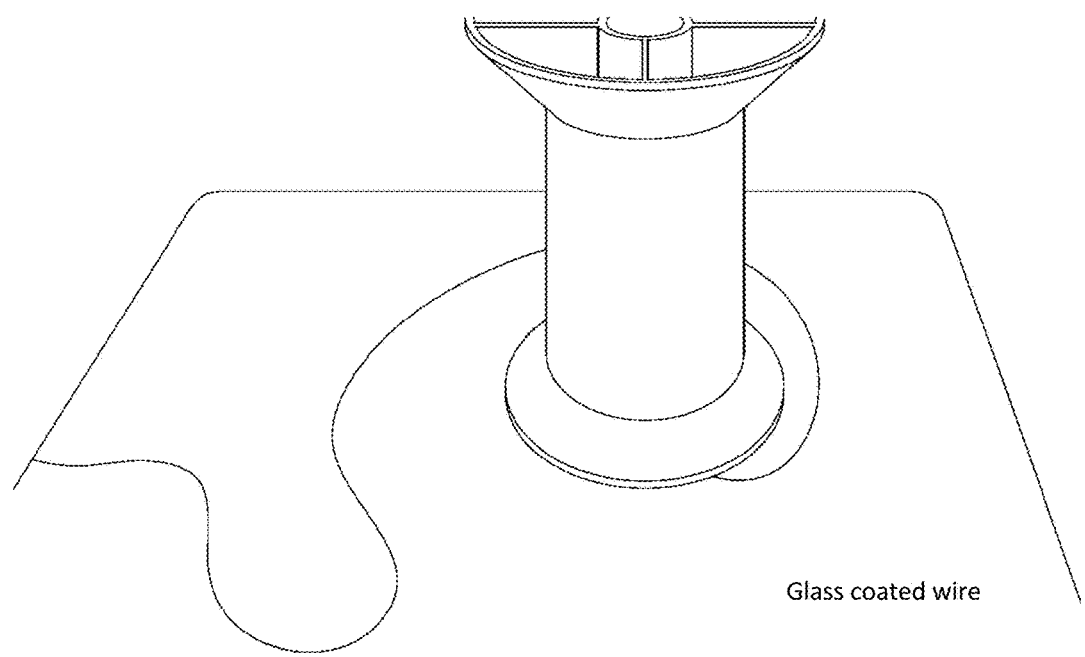
FIG. 2B is an photographic images showing the appearance of the glass-coated metal microwires practically manufactured according to an embodiment of the second method and wound around a wire bobbin.

FIG. 2B shows the appearance of the glass-coated metal microwires (cobalt-based metal core and glass shell) practically manufactured according to the second method and wound around a wire bobbin. According to the figure, the glass-coated metal microwires have a total diameter of about 60 μm in which the metal core and the glass shell are 50 μm in diameter and 10 μm in thickness, respectively.

In the embodiment, unless otherwise stated, kinds of the metal, glass material, heating temperature, cooling speed, properties of the core metal (particularly crystallinity), kinds and temperatures of the refrigerant, specific process conditions (e.g., drawing speed), dimensions of the glass-coated metal microwires, and the like are the same as described in the first method.

C. Third Method

In an embodiment of the present disclosure, the method for manufacture of glass-coated metal microwires comprises a step of drawing (stretching) a glass tube into a wire shape while heating the glass tube. Separately, metal powder may be dispersed in an ultraviolet light-curable compound (particularly a liquid phase) to afford a flowable metal dispersion which is then loaded into a capillary glass wire and exposed to ultraviolet light to cure the UV-curable compound in the dispersion, thereby producing the glass-coated metal microwires.

Figure 3A:
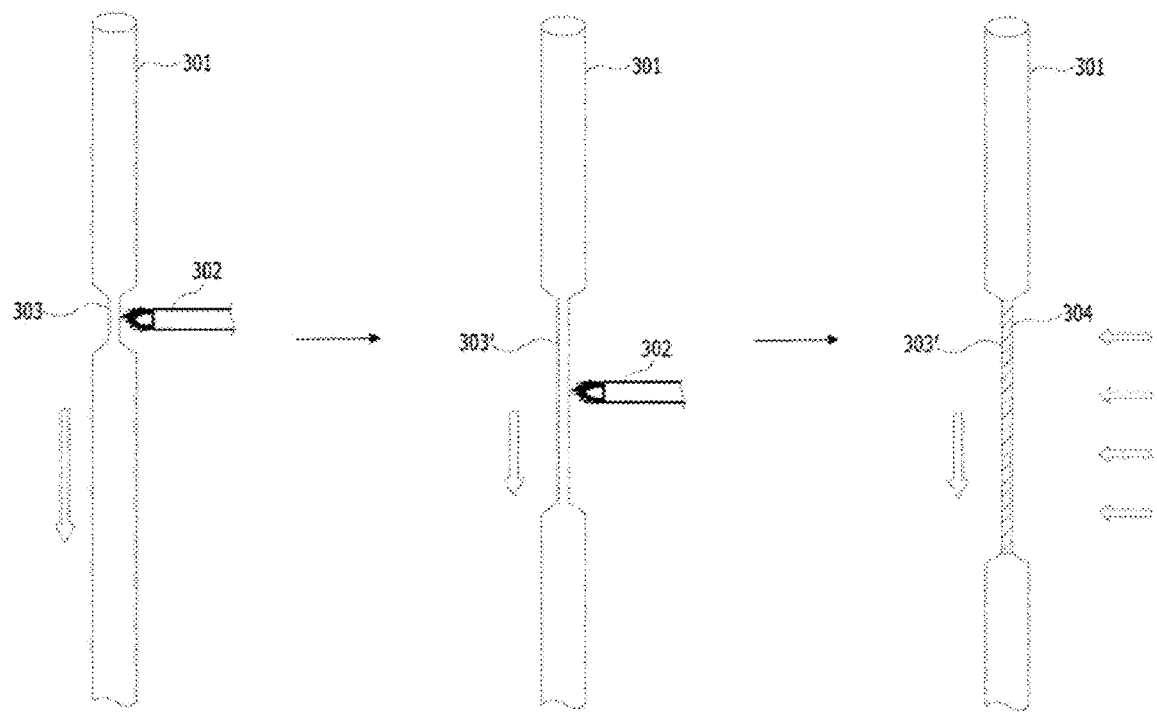
FIG. 3A is a process flow diagram illustrating an exemplary embodiment of a third method for manufacturing glass fine wires.

In this regard, FIG. 3A is a process flow diagram illustrating an exemplary embodiment of the third method for manufacture of the glass-coated metal microwires.

So long as a glass tube 301 can be formed into a glass fine wire having a desired diameter and thickness by drawing, no particular limitations of diameters (or sizes) are imparted thereto in the depicted embodiment. However, when the glass tube has too large a diameter, there may be a problem of cutting or breaking due to a local temperature difference. It may be advantageous that the glass tube have an inner diameter of, for example, about 0.2 to 2 mm, particularly about 0.3 to 1.5 mm, and more particularly about 0.5 to 1 mm (that is, capillary tube).

As the glass tube 301 is heated using a flame device 302 under the condition of applying tension in at least one of the end directions of the glass tube 301, the glass tube 301 is stretched (drawn) at the heated site. In this regard, the applied tension may range, for example, from about 1 to 10 gf, particularly from about 2 to 8 gf, and more particularly from about 3 to 5 gf.

By drawing under the application of tension, the glass tube 301 becomes lengthened at the heated site 303 so that a hollow wire with a fine inner diameter, that is, a glass fine wire 303' is formed. In this context, the drawing may be conducted in a continuous or non-continuous manner.

According to an exemplary embodiment, the glass fine wire 303' may range in inner diameter, for example, from about 50 to 200 μm, particularly from about 80 to 180 μm, and more particularly from about 100 to 150 μm. In addition, the glass fine wire 303' may have a thickness (diameter) of about 100 to 500 μm, particularly about 150 to 400 μm, and more particularly about 200 to 300 μm, which may, however, be understood to be illustrative.

Separately apart from the manufacture of the glass fine wire 303', a flowable metal dispersion for forming a core metal is prepared. The metal ingredient, as described above, may be a magnetic metal or an alloy thereof and may be additionally or alternatively, for example, copper (Cu), gold (Au), silver (Ag), iron (Fe), platinum (Pt), or a combination (or alloy) thereof. In this regard, the metal may be in a powder form wherein the metal powder may have a size (diameter) of about 10 to 100 μm, particularly about 30 to 80 μm, and more particularly about 50 to 70 μm. The metal ingredients are dispersed in an ultraviolet light-curable compound (e.g., liquid phase) to form a flowable metal dispersion.

According to an exemplary embodiment, the UV-curable compound may be a monomer, an oligomer, a polymer, or a mixture thereof in a liquid phase. In detail, the UV-curable compound may be a compound with a UV-curable functional group, for example, a polyfunctional compound with a (meth)acrylate functional group. Examples of the compound with a (meth)acrylate functional group include polyethylene glycol acrylate, polyethylene glycol diacrylate, polyethylene glycol methacrylate, acrylic acid, 2-hydroxyethyl methacrylate, 2-hydroxyethyl acrylate, 2-(2-ethoxyethoxy) enyl acrylate, tetrahydrofurfuryl acrylate, a combination thereof, etc.

According to an exemplary embodiment, the UV-curable compound may be polyethylene glycol (meth)acrylate, particularly, polyethylene glycol diacrylate, polyethylene glycol dimethacrylate, or a combination thereof.

In a particular embodiment, the UV-curable compound may be polyethylene glycol diacrylate (PEGDA) represented by the following General Formula 2:

[General Formula 2]

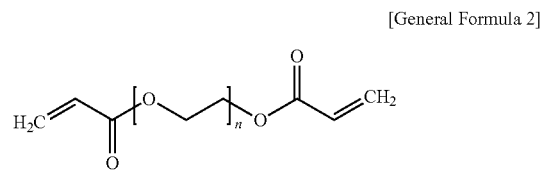

In an exemplary embodiment, polyethylene glycol diacrylate (PEGDA) may range in molecular weight (Mn), for example, from about 100 to 1000, particularly from about 150 to 800, and more particularly from about 200 to 600. The UV-curable compound may be in a liquid phase with a viscosity (25° C.) of, for example, about 30 to 80 cps, particularly about 40 to 70 cps, and more particularly about 45 to 65 cps.

According to an exemplary embodiment, the content of metal powder in the flowable metal dispersion may range, for example, from about 50 to 90% by weight, particularly from about 60 to 80% by weight, and more particularly from about 65 to 75% by weight. Too large a content of metal powder does not allow a desired level of flowability to be secured so that the metal powder is difficult to load into the glass fine wire that is being drawn. On the other hand, when the metal powder is used at too small a content, the resulting small amount of metal contained in the glass fine wire makes it difficult to obtain a desired level of magnetism in the non-spherical/asymmetric fine particles to be prepared later. Thus, a metal content within the above-mentioned range may be advantageous, but the range is illustrative and may change according to kinds of metal and dispersion media.

In addition, the dispersion may be optionally added with a photoinitiator, a crosslinking agent, etc. Examples of such a photoinitiator include benzophenone, 4-methylbenzophenone, benzoyl benzoate, phenylacetophenone, 2,2-dimethoxy-2-phenylacetophenone, α,α-diethoxyacetophenone, hydroxycyclo-hexylphenylketone, 2-hydroxy-2-methyl-1-phenylpropan-1-one, bis-(2,6-dimethoxybenzoyl)-2,4,4-trimethylpentyl phosphine oxide, 2-hydroxy-2-methyl-1-phenylpropan-1-one, 2,4,6-trimethylbenzoyl-diphenylphosphine oxide, or a combination thereof. In addition, N, N'-methylene bisacrylamide, methylene bismethacrylamide, ethylene glycol dimethacrylate, or a combination thereof may be used as a crosslinking agent. Such optional additives may be used in an amount of, for example, about 0.1 to 10% by weight, particularly about 0.5 to 5% by weight, and more particularly about 1 to 3% by weight, based on 100 parts by weight of the flowable metal dispersion.

The flowable metal dispersion 304 prepared separately is loaded (or injected) into the glass fine wire 303'. For example, the dispersion 304 may be loaded into the inner space of the glass wire having a fine diameter in a micro-injection manner using a capillary phenomenon or a syringe.

After the flowable metal dispersion 304 is loaded into the glass fine wire 303' as described above, the dispersion is exposed to UV light to cure the UV-curable compound in the dispersion. At this time, the UV intensity may range, for example, from about 60 to 2,000 mW/cm2, particularly from about 300 to 1,700 mW/cm2, and more particularly from about 400 to 1,500 mW/cm2. For example, the UV intensity may be about 67 mW/cm2 for a 4× lens, 420 mW/cm2 for a 10× lens, and 1670 mW/cm2 for a 20× lens.

As such, the metal-containing dispersion in the glass fine wire 303' is cured by UV light to form a solidified metal-containing core and thus to manufacture the glass-coated metal microwires. In this regard, the diameter of the metal core may correspond to the inner diameter of the glass fine wire 303'.

Figure 3B:
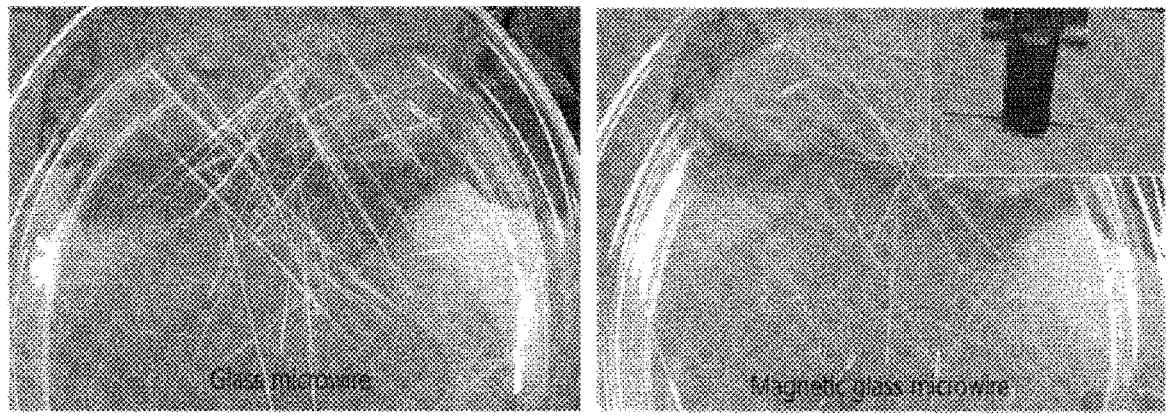
FIG. 3B shows photographic images of the appearances of 100 mm-long fragments cut from the glass fine wires and the glass-coated metal microwires manufactured by charging the glass fine wire with the flowable magnetic metal dispersion and curing the compound, which were practically prepared according to an embodiment of the third method.

FIG. 3B shows the appearances of 100 mm-long fragments cut from the glass fine wire (glass material: borosilicate) and the glass-coated metal microwires manufactured by charging the glass fine wire with the flowable metal dispersion (metal: $Fe_3O_4$, UV-curable compound: PEGDA) and curing the compound, which were practically prepared according to the third method. According to the figure, the glass-coated metal microwires have a total diameter of about 90 μm in which the metal core and the glass shell are 70 μm in diameter and 20 μm in thickness, respectively.

One of the advantages of the third method is to simultaneously conduct a coding step such as barcode formation and the process of manufacturing a glass-coated metal microwire. According to an exemplary embodiment, when the flowable metal dispersion 304 is exposed in a particular pattern to UV light after being loaded into the glass fine wire 303', a specific security or certification pattern can be formed for the exposed portions. That is, codes corresponding to UV light exposure patterns can be formed in a core region within the glass-coated metal microwires.

Next, as will be described later, the security or certification codes formed at predetermined intervals in the core of the glass-coated metal microwires are cut with laser to prepare coded non-spherical/asymmetric fine particles. Thus, an additional code treatment step may be omitted.

MODE FOR THE INVENTION

Preparation of Non-Spherical/Asymmetric Fine Particles

According to one embodiment of the present disclosure, a process of cutting the fine wire manufactured as described above is performed to prepare non-spherical/asymmetric fine particles. In this regard, FIG. 4 shows the appearance of a laser cutting system for processing fine wires to produce non-spherical/asymmetric fine particles and FIG. 5 schematically illustrates the fixation of fine wires at accurate positions onto a wire holder prior to laser cutting.

As shown, this embodiment provides the advantage that a plurality of fine wires is arranged in a traverse direction (for example, in parallel) and cut into a predetermined length to produce non-spherical/asymmetric fine particles with large-scaled quantity. For this, a cutting method using non-contact laser is adopted.

Figure 4:
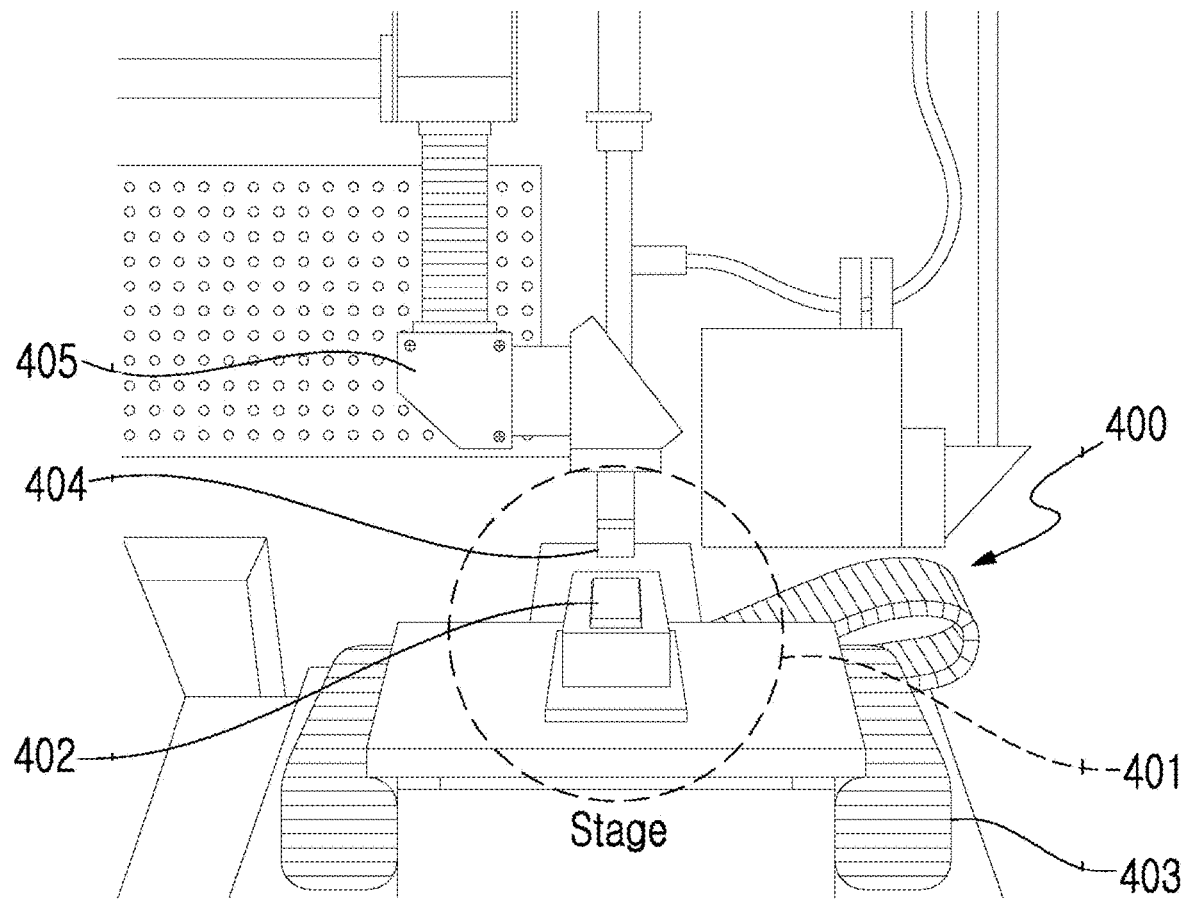
FIG. 4 is a photographic image showing the appearance of a laser cutting system for machining fine wires to produce non-spherical/asymmetric fine particles.
Figure 5:
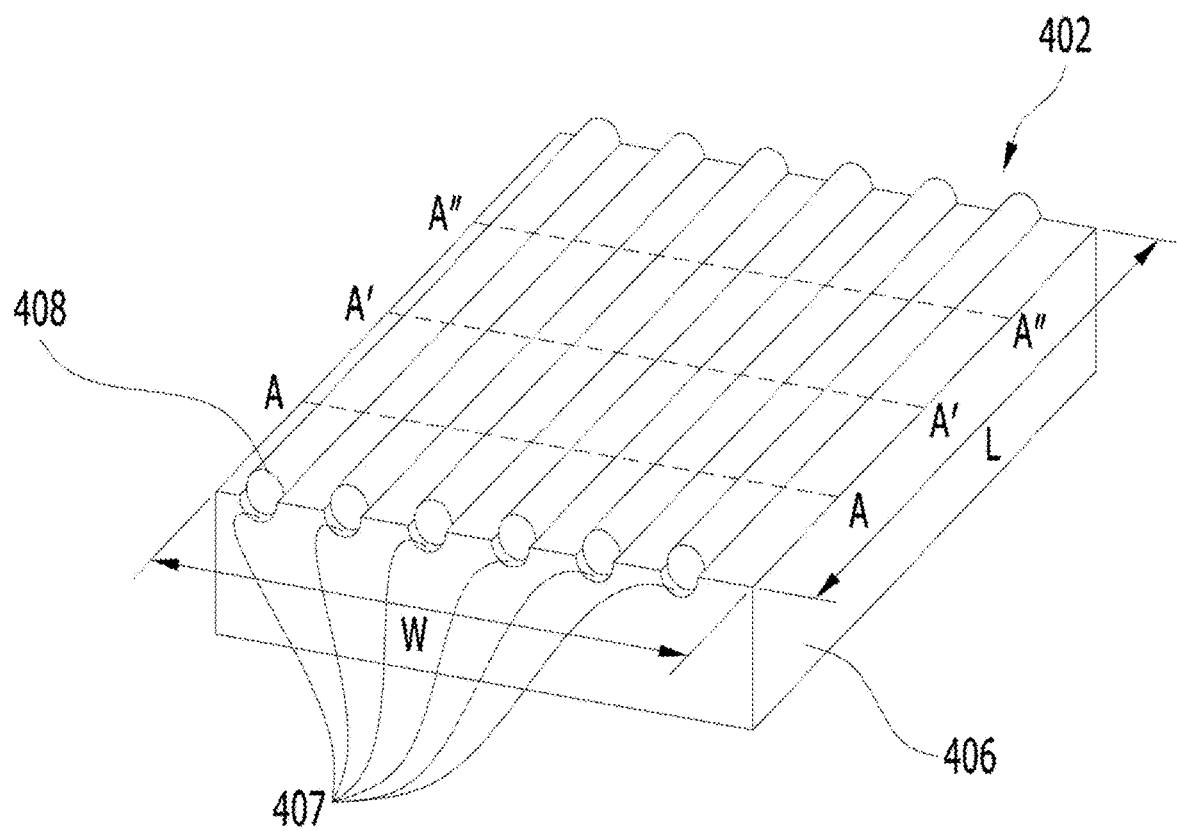
FIG. 5 is a schematic view illustrating the fixation of fine wires at accurate positions onto a wire holder prior to laser cutting.

With reference to FIG. 4, a laser machining system 400 generally comprises a processing stage 401 for processing fine wires and a laser irradiator 404. In the embodiment depicted, a wire holder 402 for fixing fine wires thereonto is positioned on the processing stage 401 and a position controller 403 that is electrically operated to control the stage in xyz directions to an accurate position is provided under the stage 401.

Meanwhile, a laser irradiator 404 is positioned at a distance from (non-contact with) the wire holder 402 above the stage 401 and may be mounted under a locomotion member 405 configured to move in particular directions with at least a particular gap arranged thereto.

Referring to FIG. 5, the wire holder 402 have a plurality of grooves 407 arranged in a traverse (or width) direction on a main body portion 406 thereof. According to an exemplary embodiment, even though not particularly limited, the material of the wire holder may be advantageously a rubber magnetic material so as for the fine wires 408, especially magnetic metal core-containing fine wires to be immobilized at desired positioned without being scattered.

In the depicted embodiment, the size of individual grooves 407 and the distance between multiple grooves 407 may be appropriately controlled in consideration of the diameter of the fine wire 408 to be processed. In this regard, the distance between the multiple grooves may be determined within the range of, for example, about 0.1 to 2 mm and particularly about 0.2 to 1 mm, but is not limited thereto. In addition, the depth of the groove 407 may be any dimension at which the fine wires 408 do not substantially move during the laser cutting process. For example, the grooves may be about 30 to 500 μm, particularly about 50 to 400 μm and more particularly about 100 to 300 μm deep from the upper surface of the wire holder 402.

In this embodiment, at least one but preferably multiple fine wires 408 are immobilized in the grooves 407 of the wire holder 402 and positioned on the stage 401 for laser machining. Next, the laser irradiator 404 cuts and machines the fine wires 408 while moving in traverse directions, in detail, along the paths A-A, A'-A', and A"-A", which are apart from each other in sequence at a predetermined gap, with the controlled motion or movement of the laser locomotion member 405.

An ultrafine laser technique may be applied to a laser available in this embodiment. As such, a laser source must supply sufficient energy to cut the glass coat (shell) and metal core constituting the fine wires 408 within a short time by the irradiation of laser during the movement of the laser irradiator 404. Particularly, it is advantageous to employ a laser capable of machining at a nano- or micro-level.

According to an exemplary embodiment, an infrared (e.g., $CO_2$ laser), near-infrared laser diodes (DPSS), a femto-second laser, etc. may be applied. A $CO_2$ laser adopts a laser beam-evoked thermal machining manner in which a beam of $CO_2$ laser light is absorbed onto the surface of a target and converted into heat so that the generated heat energy machines the target by melting a region of interest. A high energy is required for CO-laser cutting and machining because the reflectivity of the laser beam is high. Taking this into consideration, a femto-second laser may be used for cutting and machining the fine wires because the resulting non-spherical/asymmetric fine particles are allowed to have uniform properties.

In addition, it may be required that a laser having a pulse width shorter than the heat propagation time of the fine wires that is being cut is used for cutting and machining without any thermal damage and structural change in the fine wires. When machined with lasers having short pulse widths, fine wires are cut at local portions within a very short time without a heat diffusion phenomenon and with almost no molten regions remaining, whereby precise machining can be performed without surface damages, compared to conventional laser thermal machining processes.

Particularly, for femto-second pulses, the heat diffusion duration is less than nano-second so that ablation is conducted prior to the formation of a plasma or fluid field, thereby significantly suppressing the reduction of machining precision that is caused by the formation of thermally influenced portions and the fluid dynamic effect. In addition, very short pulses in femto-second unit allows the power density of a focusing plane to be increased to a level of 1015 W/cm$^2$ or higher. Such high irradiation intensity may principally change interaction between laser and materials and induce new phenomena in various aspects.

According to one embodiment, the laser used for cutting may vary in wavelength. For example, a pulse-type laser with a wavelength of about 300 to 1,200 nm, particularly about 343 to 1,028 nm, and more particularly about 400 to 900 nm may be used. Furthermore, such a laser is advantageous in that a molten matter and debris formed around the subject upon the application of a conventional laser is not generated and, even if generated, is in the very fine powder form which can be easily removed. In addition, the pulse width of the laser may vary and may be, for example, about 290 fs or less, particularly about 1 to 250 fs, and more particularly about 10 to 200 fs. In this regard, the pulse-type laser may have a pulse energy of, for example, about 1 to 400 µJ, particularly about 5 to 200 µJ, and more particularly about 10 to 100 µJ. Further, the beam width of the laser may be about 15 µm or less, particularly about 0.5 to 10 µm and more particularly about 1 to 5 µm.

According to an alternative embodiment, the laser pulse width may vary according to the material of the subject to be processed and may range, for example, from about 290 fs to 10 ps.

According to an exemplary embodiment, the stage 401 may move a distance of up to, for example, about 5,000 mm, with an interval precision of movement of about 1 µm. The distance and the interval of movement can be suitably chosen depending upon materials and dimensions of the fine wires.

Meanwhile, the gap between the paths (A-A, A'-A', and A"-A") can be determined according to a desired aspect ratio of the non-spherical/asymmetric fine particles. In this context, the aspect ratio may range from about 2 to 15. In one embodiment, the aspect ratio may range from about 3 to 5 for a microrod shape. In another embodiment, a microbar may have an aspect ratio of about 5 to 10.

Because at least one fine wire can be cut within a short time even with a simple operation of irradiating laser in a stepwise manner according to predetermined intervals, desirable non-spherical/asymmetric fine particles can be produced in large-scaled quantity. Therefore, remarkably increased productivity of fine particles can be achieved, compared to conventional production methods for non-spherical/asymmetric fine particles.

In addition, the metal core and the glass coat can be dimensionally controlled upon the manufacture of fine wires and non-spherical/asymmetric fine particles of desired shapes (or morphologies) and sizes can be produced by adjusting intervals of laser emission during laser machining.

Figure 6:
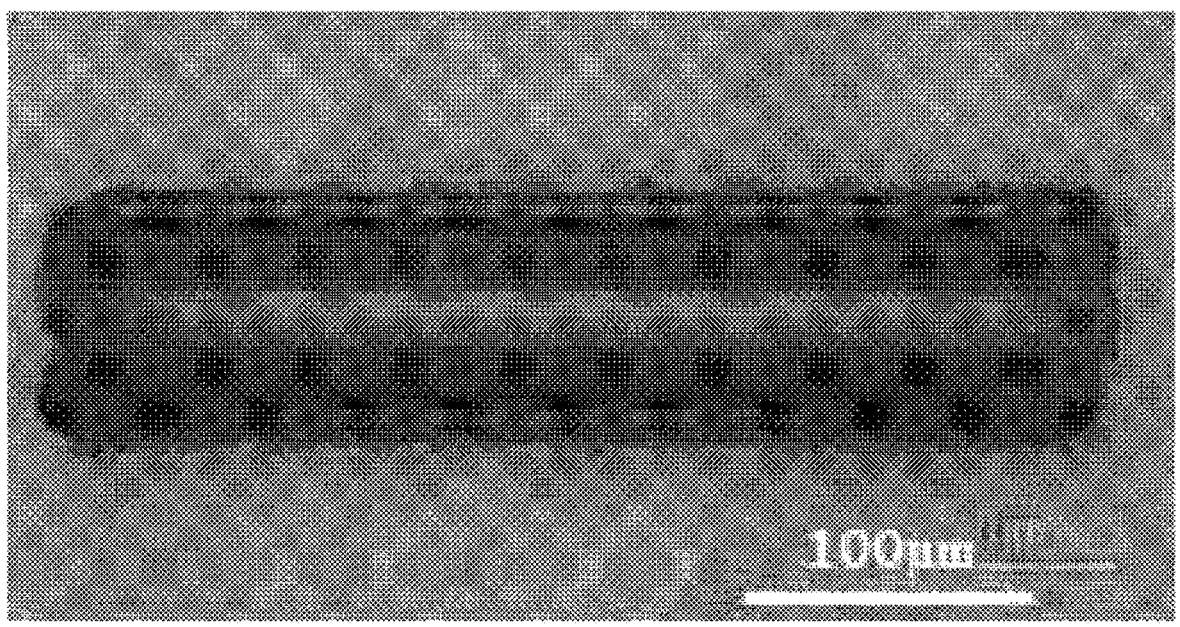
FIG. 6 is an optical microscope image (20-fold magnification) of the non-spherical/asymmetric fine particles obtained by laser cutting the glass-coated metal microwires manufactured according to the first method with the aid of the machining device shown in FIG. 4.

The glass-coated metal microwires manufactured according to the first method was subjected to laser cutting using the machining device shown in FIG. 4 (laser source: CARBIDE 5W femtosecond laser; laser wavelength: 1028 nm; Power: 5W; laser pulse width: <290 fs; stage: 500×500 mm; stage step: 1 µm resolution). An optical microscope image (20-fold magnification) of the microrod-shaped non-spherical/asymmetric microparticle thus obtained is shown in FIG. 6. The fine particles were 400 µm long on average with an aspect ratio of 5.7.

Figure 7A:
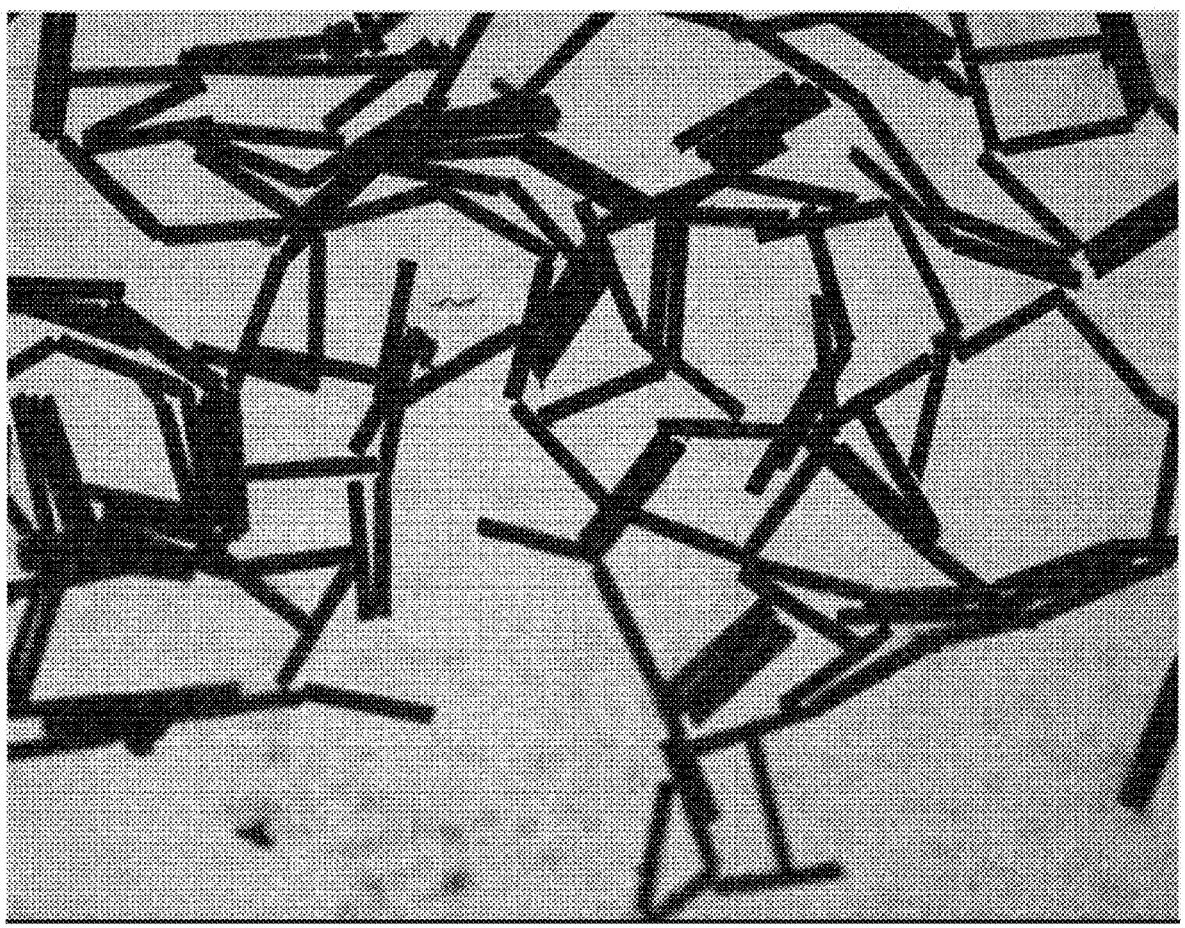
FIGS. 7A and 7B are optical microscope images (4- and 20-fold magnification, respectively) of the non-spherical/asymmetric fine particles obtained by laser cutting the glass-coated metal microwires manufactured according to the second method, with the aid of the machining device shown in FIG. 4.
Figure 7B:
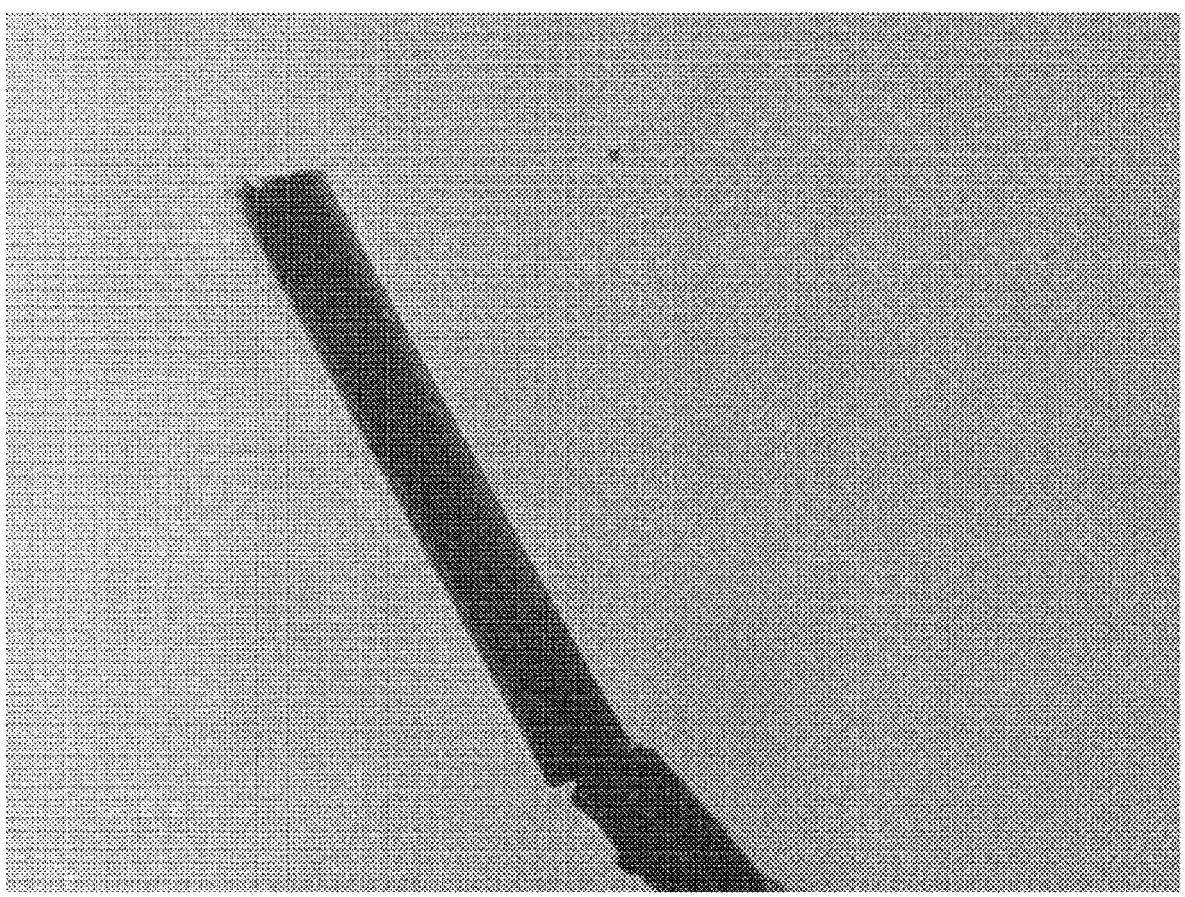

FIGS. 7A and 7B show optical microscope images (4- and 20-fold magnification, respectively) of the non-spherical/asymmetric fine particles obtained by using the machining device shown in FIG. 4 to laser cut the glass-coated metal microwires manufactured according to the second method. The fine particles were measured to have an average length of 400 µm with an aspect ratio of 5.7.

Figure 8:
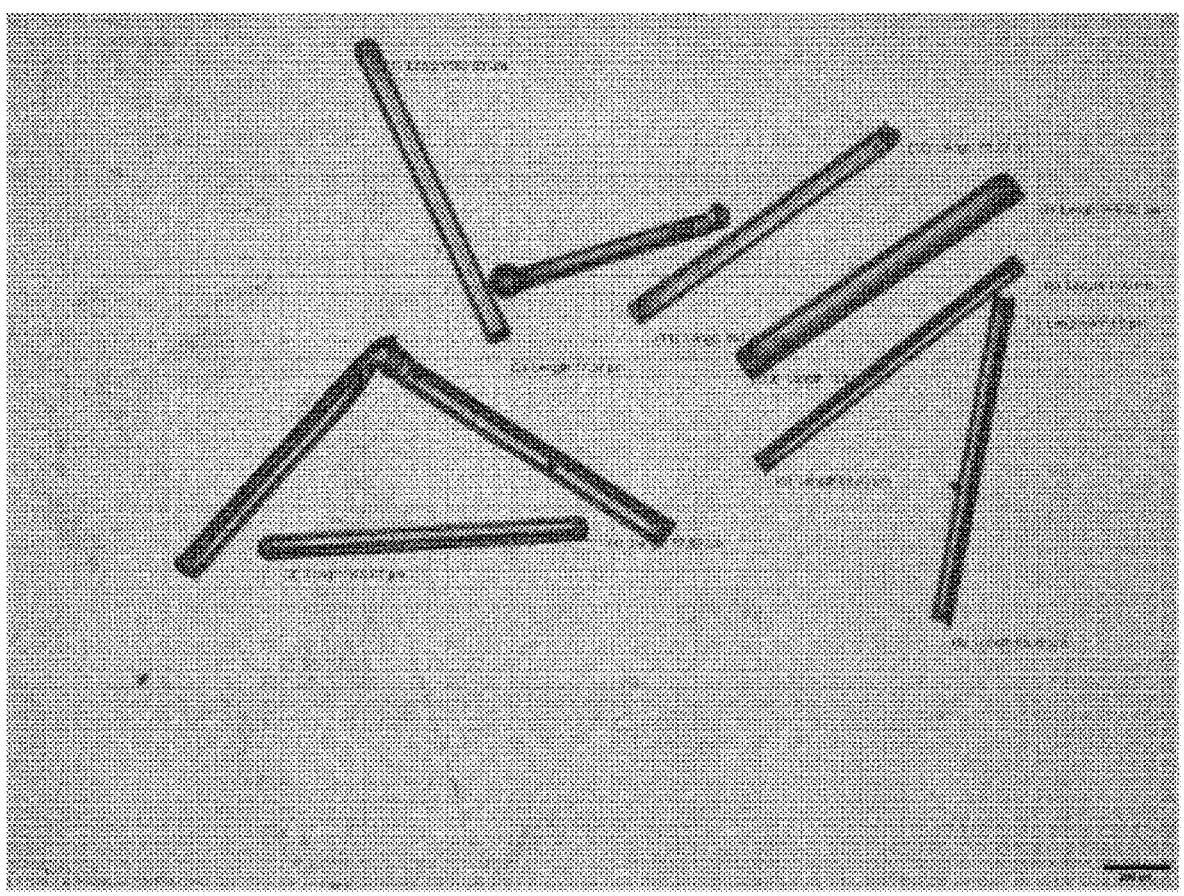
FIG. 8 is an optical microscope image (4-fold magnification) of various non-spherical/asymmetric fine particles obtained by laser cutting cut the glass-coated metal microwires manufactured according to the third method with the aid of the machining device shown in FIG. 4.

An optical microscope image (4-fold magnification) of the non-spherical/asymmetric fine particles obtained by using the machining device shown in FIG. 4 to laser cut the glass-coated metal microwires manufactured according to the third method is shown in FIG. 8. The fine particles were 1,000 µm on average with an aspect ratio of about 10 to 11.

Use of Non-Spherical/Asymmetric Fine Particles

Non-spherical/asymmetric fine particles formed by laser cutting as described above can substitute for conventional spherical fine particles. Bioassay and security (or certification) are representative of the fields to which the non-spherical/asymmetric fine particles can be applied.

A. Use in Bioassay

In an exemplary embodiment where the non-spherical/asymmetric fine particles are applied to a bioassay, a magnetic metal responsible for the core upon the manufacture of the fine wire may provide various advantages. For an in-vitro diagnostic device, which requires a process of enriching a biomaterial in a sample, magnetic ingredient-containing fine particles to which a biomaterial is fixed (bound or attached) can be rapidly separated by applying an external magnetic field with the aid of a simple magnet and can be applied to diagnosis. As such, the fine particles allow for easy separation of specific target molecules or cells from complex matrices and thus are advantageous for washing and enriching target ingredients or biomaterials.

In a particular embodiment, a paramagnetic metal may be used as the core metal. Thanks to the characteristic magnetism thereof, the fine particles containing such a paramagnetic metal enable DNA/RNA, proteins, antibodies, fluorescent substance, cells, and the like to bind to (or associate with) or to separate from the surface thereof. Hence, the fine particles can find a wide spectrum of applications to biomaterial separation, MRI contrast, target drug delivery, biosensors, and the like.

In addition, the non-spherical/asymmetric fine particles can stably exhibit non-specific binding properties due to the glass-coated layer or glass-containing surface. As used herein, the term "specific reaction" means specificity of a binding reagent, for example, an antibody, that is, preferential reaction or binding to a specific material. Thus, because a specific reaction is based on the reaction or binding of only a specific material in a sample, for example, specific binding properties in a protein detection system for molecular diagnosis may be disadvantageous in immobilizing various functional groups. However, the non-spherical/asymmetric fine particles can immobilize various functional groups thereto because the surface thereof exhibits non-specific binding properties (surface treatment). In addition, the glass ingredient in the non-spherical/asymmetric fine particles can suppress the absorption of external biomolecules into the fine particles, thus enabling accurate diagnosis.

Moreover, when the core metal contains a magnetic material, effective improvement can be brought about in the particle-based diagnosis performance. In a sandwich-typed assay, for example, grafted particles (e.g., particles grafted to a DNA strand for capturing a specific nucleotide sequence) can be rapidly enriched by magnetic actuation.

As described, the non-spherical/asymmetric fine particles can provide a magnetic matrix applicable to protein purification, proteomics, genetic fields, etc. In this regard, for example, functional groups of disease labeling materials (e.g., —COOH, —NH—, —OH, —SH, —CHO, $C_4$-$C_{18}$ hydrocarbon groups, tosyl group, etc.), streptavidin, protein A, protein G, antibodies for immunoassay reagent, such as anti-mouse IgG (e.g., goat anti-mouse IgG antibody), and/or other ligand-specific molecules (e.g., binders for detecting diagnostic reagents) can be immobilized or applied to the surface of the fine particles.

According to an exemplary embodiment, various functional groups or binders bound to the surface of the fine particles allow for diagnosis or detection in various ways using labeling materials (or signaling materials). Illustrating examples of the labeling materials include metal nanoparticles (e.g., gold, silver, copper nanoparticles), quantum dot nanoparticles, magnetic nanoparticles, enzymes, enzyme substrates, enzymatic reaction products, light absorption substance, phosphorescent materials, and luminescent materials. More particularly, the labeling material may be a phosphorescent material, as exemplified by fluorescein dyes inclusive of umbelliferone, fluorescein, fluorescein isothiocyanate (FITC), rhodamine, TAMRA, dichlorotriazinylamine fluorescein, dansyl chloride, quantum dots, phycoerythrin, and FAM (fluorescein amidite), alexa fluor, and cyanine dyes inclusive of Cy3, Cy5, Cy7, and indocyanine green. These dyes may be used alone or in combination. In addition, phosphorescent material-containing phosphorescence fine particles or nanoparticles may be used alone or in combination. In this regard, a fluorescent material is excited by light of a specific wavelength and emits light of a different wavelength to discharge extra energy. FITC, fluorescein, and Cy3 emit light having wavelengths of 550 nm, 520 nm, and 570 nm, respectively.

Figure 9A:
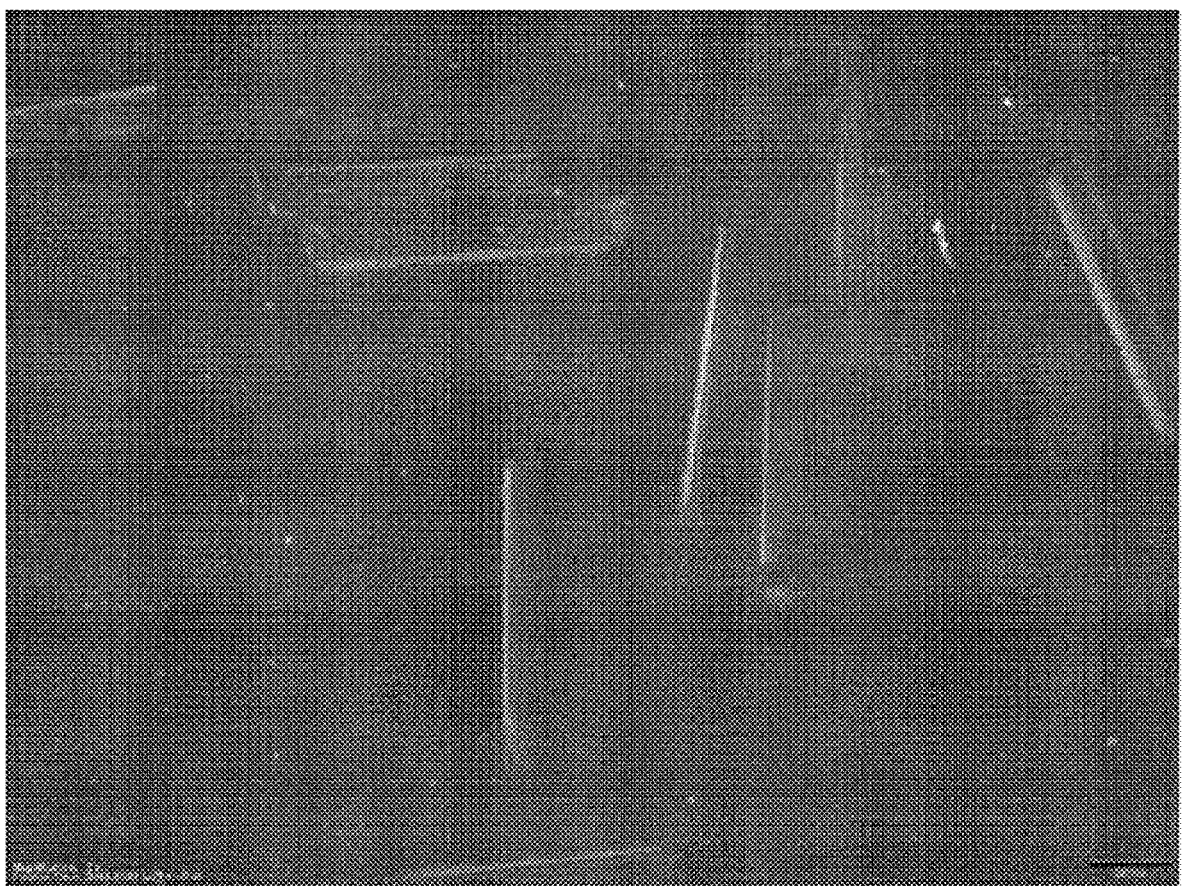
FIGS. 9A and 9B, respectively, are a bright field microscope and a green fluorescence microscope image (filter band: 590 nm) of the non-spherical/asymmetric fine particles which have been labeled with FITC on the surface chemistry of amine ($-NH_2$) that are coated by an APTES ((3-aminopropyl)triethoxysilane) solution and coupling the ethoxysilane group of APTES with hydroxy group ($-OH$)
Figure 9B:
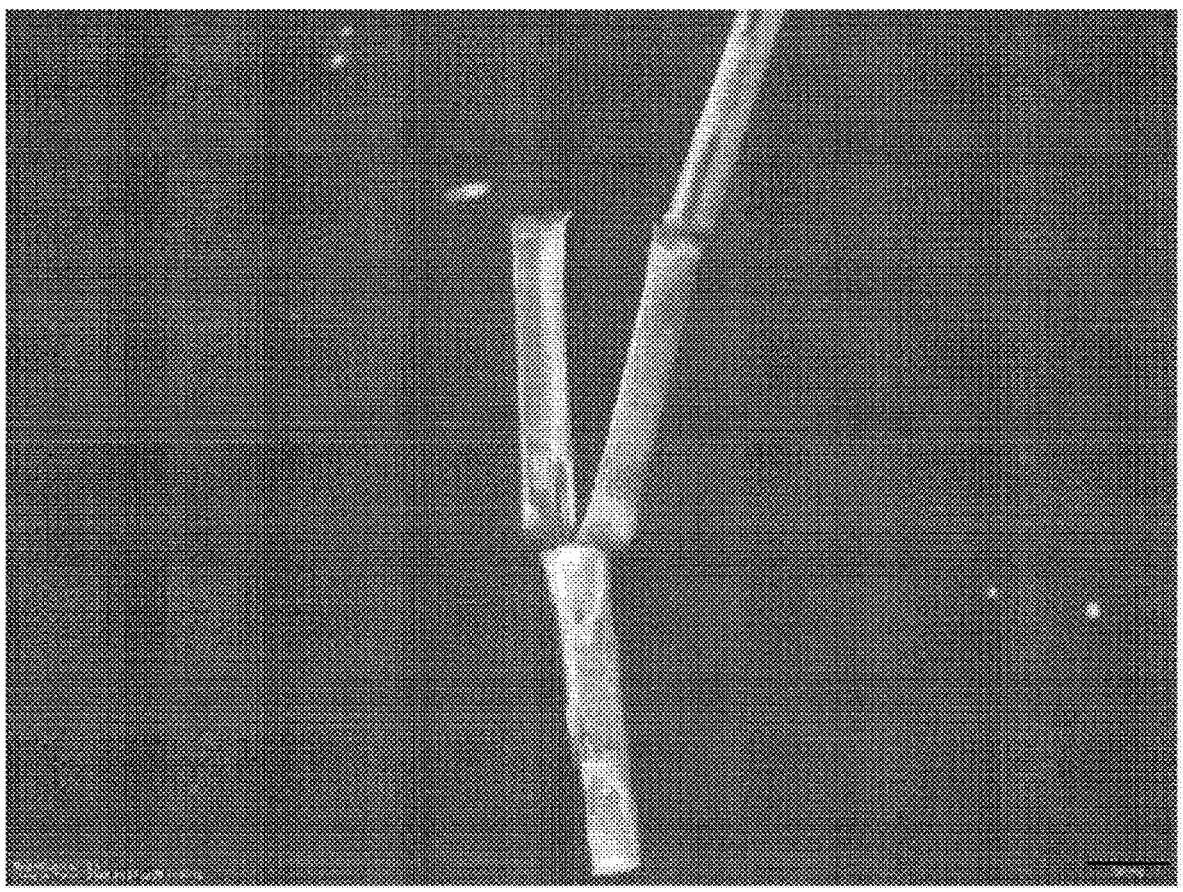

FIGS. 9A and 9B are images of magnetic glass-coated fine particles (one of the non-spherical/asymmetric fine particles) which have been labeled with FITC on the surface chemistry of amine (—$NH_2$) that are coated by an APTES ((3-aminopropyl)triethoxysilane) solution and coupling the ethoxysilane group of APTES with hydroxy group (—OH). According to the figures, the fluorescently labeled fine particles can be observed to emit green light under a fluorescence microscope.

FIGS. 10A to 10D are images of magnetic glass-coated fine particles (one of the non-spherical/asymmetric fine particles) that have undergone a fluorescent immunostaining reaction using an antigen-antibody reaction. In detail, the surface of non-spherical/asymmetric fine particles is subjected to an antigen-antibody reaction using mouse serum (primary antibody) and goat anti-mouse IgG-biotin (secondary antibody), followed by fluorescent immunostaining with biotin and streptavidin-fluorescent body (PE, PE-eFluore 610, alexa 568).

Streptavidin, which is a protein isolated from the bacterium *Streptomyces avidinii*, has high affinity for biotin and does not bind to lectin because it is not a glycoprotein. Biotin is a kind of vitamin, particularly, a B-complex vitamin (hexahydro-2-oxo-1H-thieno [3,4-d]imidazoline-4-valeric acid) that is composed of a ureido (tetrahydroimidizalone) ring fused with a tetrahydrothiophene ring, with a molecular weight of about 244 g/mol. A valeric acid substituent is attached to one of the carbon atoms of the tetrahydrothiophene ring. Biotin has high affinity for and can specifically bind streptavidin. For example, four biotin molecules can bind to one streptavidin molecule.

With reference to FIGS. 10A and 10B, PE (phycoerythrin) fluorescent material was observed to be expressed on fluorescence microscope images as a result of the fluorescent immunostaining reaction (goat anti mouse IgG-biotin and streptavidin-PE (phycoerythrin)).

Referring to FIGS. 10C and 10D, there are results of non-immunoreaction with mouse serum and goat antimouse immunoglobulin. As can be seen, the bright-field microscope image of FIG. 10C is not substantially different from the image of FIG. 10A, but no fluorescent materials were expressed (non-fluorescent reaction) on the fluorescence microscope image (FIG. 10D).

FIG. 11 shows diagnosis (or detection) using two fluorescent materials bound to the surface of the surface-modified non-spherical/asymmetric fine particles. As shown in the figure, the non-spherical/asymmetric fine particles according to an embodiment of the present disclosure can be applied for bio-diagnosis.

Bio-diagnosis using non-spherical/asymmetric fine particles may be exemplified by particle diagnosis. In this case, a colloidal suspension of antibody-coated particles is used. When an antigen is contained in a sample, the particle antibody binds to the antigen to form a sandwich complex between two particles (specific aggregation). This particle aggregation changes optical properties of the system. For a simple diagnosis, the change can be detected with the naked eye. For higher sensitivity, advantage can be taken of light scattering or turbidity according to particle sizes or concentrations (a change in absorption or scattering is proportional to a degree of aggregation associated with a specimen). That is, a high concentration of an antigen in a sample allows for the formation of large particle clusters. Compared to general particles, particularly non-spherical/asymmetric fine particles containing magnetic core metal are more apt to aggregate in the presence of a magnetic field and thus can remarkably reduce a diffusion time required for a specific reaction between particles.

According to an exemplary embodiment, the non-spherical/asymmetric fine particles may be advantageously applied to a point-of-care (POC) platform that can detect a target material in a small amount of a sample rapidly and accurately, for example, an endocrine sex hormone test device. In detail, the ratio between testosterone and estradiol (T/E2), which are the major male sex hormone and the major female sex hormone, respectively, corresponds to an important factor in hormone balance. The probability of onset of prostate cancer in men increases with decreasing of the level of testosterone. Injection of testosterone stops the growth of the cancer cells. These facts support that testosterone suppresses the onset and development of prostate cancer.

Therefore, the fine particles can be used as a matrix or substrate onto which antibodies to sex hormones (testosterone and estradiol) are immobilized. In this case, non-spherical/asymmetric fine particles may be prepared to have various sizes or morphologies for discriminated sales and high commercialization.

According to a particular embodiment, a step of modifying the surface of the glass coat layer of the non-spherical/asymmetric fine particles may be optionally conducted. Such modification allows the introduction of a carboxyl group and/or an amine group onto the surface and these optional functional groups make it possible to bind the particles to more various biomaterials.

B. Use in Security (Certification) Field

According to another embodiment of the present disclosure, the non-spherical/asymmetric fine particles prepared by the above-mentioned methods can be used for security or certification purposes. In detail, the surface of the fine particles may be indexed or coded (or codes may be inserted or formed). In an exemplary embodiment, codes introduced onto the non-spherical/asymmetric fine particles may be cryptic codes, particularly, encoded one-dimensional barcodes. As such, the coded fine particles may be incorporated to surfaces or insides of various substrates or materials. Examples of such substrates or materials include paper, paperboards, foil, paper laminates, plastics, polymers, and fibers (e.g., yarns, threads, fabrics, etc.). Special clothes, security papers, etc. can be made by incorporating the coded fine particles, particularly, fine particles containing magnetic ingredients therein into fabrics, paper, etc.

Various conventional encoding techniques used in the optical fiber field can be applied to the non-spherical/asymmetric fine particles. In this context, various information can be stored in the coded glass-coated layer. For example, at least one of the properties of the glass coating including index of reflection, surface reflectance, transmissivity, fluorescence, and the like can be modified.

A photolithography technique can be applied to encoding the non-spherical/asymmetric fine particles, thereby patterning graphic codes. In this regard, the patterning of graphic codes may be achieved by inserting binary codes into the fine particles or by a patterning technique using photolithography known in the art. According to another embodiment, the non-spherical/asymmetric fine particles may be coded in such a manner that fluorescent materials with different colors are introduced into the non-spherical/asymmetric fine particles. For introduction of various fluorescent materials into fine particles, an incorporation technique known in the art may be employed.

According to an exemplary embodiment, the glass coating of each fine particle exhibits a specific distinguishable color (intrinsic color, or fluorescence expressed by light). For an intrinsic color, optical properties of the glass coat can be determined by chemical compositions. Therefore, while a specific basic color is provided, a variety of colors may be expressed by incorporating dopants (e.g., rare earth metals). Hence, detectable characteristic labels can be provided through a combination with dopants. For fluorescence expressed by light is used, when light having a particular wavelength is incident on the surface of the glass, light having a wavelength longer than that of the incident light is emitted, generating fluorescence from the glass. Thus, desired fluorescent light can be generated by adjusting a glass composition and can be used as an identification label.

According to another embodiment, the fine particles can be coded by introducing multi-bit optical codes (in detail, optical barcodes) onto the surface thereof. Such optical barcodes can be detected using devices known in the art (e.g., red laser scanner, etc.). Alternatively, a method of detecting specific optical wavelengths can be utilized and provide an additional security effect due to difficulty in counterfeiting and falsification. Examples of the aforementioned barcode formation technique are as follows: (i) a process in which ink is printed on fine particles and cured by UV exposure or heating to form barcodes on the surface of the particles, (ii) a process in which the surface of particle is exposed to specific laser to alter reflectance on the exposed region and the reader of the altered values is used together, or a laser is used to directly form optical barcode patterns on the surface of particle, and (iii) a process in which a uniform coat layer is formed on the surface of particle and cured while optically readable barcodes are patterned, and this process may be combined with lithography.

FIG. 12 shows surfaces of coded non-spherical/asymmetric fine particles. As shown in the figure, non-spherical/asymmetric fine particles have digital barcodes formed on the surfaces thereof and can be used for identification.

Among the above-described methods for manufacturing the glass-coated metal microwires, the UV irradiation (the third method) employs patterned UV irradiation, which allows for the omission of a separate coding process.

A method in which the glass-coated metal microwires are manufactured according to embodiments of the present disclosure and then subjected to laser machining to produce non-spherical/asymmetric fine particles and a conventional technique (in detail, hydrogel particle process using a photomask) were compared for output per hour and the results are given in Table 1, below.

TABLE 1

|  | Particle | Output |
|---|---|---|
| Hydrogel particle process using photomask (conventional) | 500 μm cylindrical (height: 100 μm) | 54,000 particles/hour |
| Laser cutting process using glass-coated meta wires (automatic) | Fine rod (diameter: 70 μm, length: 400 μm) | 2,500,000 particles/hour |

As is understood from the table, the method for producing non-spherical/asymmetric fine particles according to the present disclosure can achieve the effect of greatly increasing productivity, compared to conventional techniques. While the present invention has been described with respect to the specific embodiments, it will be apparent to those skilled in the art that various changes and modifications may be made without departing from the spirit and scope of the invention as defined in the following claims.

The invention claimed is:

1. A method for production of non-spherical/asymmetric fine particles, the method comprising the steps of:
   filling a glass tube with a metal;
   drawing the metal-filled glass tube while melting a lower portion of the glass tube by heating;
   cooling the drawn melt to form at least one glass-coated metal microwire;
   positioning the at least one glass-coated metal microwire in at least one of a plurality of grooves arranged in a width direction on a wire holder; and
   cutting the at least one glass-coated metal microwire positioned on the wire holder, in a traverse direction at a predetermined distance in a non-contact machining process using a laser having a pulse width shorter than the heat propagation time of the at least one glass-coated metal microwire to produce non-spherical/asymmetric fine particles, wherein the total diameter of the at least one glass-coated metal microwire ranges from 50 to 200 μm, and wherein the aspect ratio of nonspherical/asymmetric fine particles ranges from 2 to 15.

2. A method for production of non-spherical/asymmetric fine particles, the method comprising the steps of:
   melting a metal by heating while separately heating a glass material to a temperature at which the glass material is drawable;

drawing the heated glass material while loading the melted metal to an inside of the glass material;

cooling the melted metal-loaded, drawn glass material to form at least one glass-coated metal microwire;

positioning the at least one glass-coated metal microwire in at least one of a plurality of grooves arranged in a width direction on a wire holder; and cutting the at least one glass-coated metal microwire positioned on the wire holder, in a traverse direction at predetermined distance gaps in a non-contact machining process using a laser having a pulse width shorter than the heat propagation time of the at least one glass-coated metal microwire to produce non-spherical/asymmetric fine particles, wherein the total diameter of the at least one glass-coated metal microwire ranges from 50 to 200 μm, and wherein the aspect ratio of nonspherical/asymmetric fine particles ranges from 2 to 15.

3. A method for production of non-spherical/asymmetric fine particles, the method comprising the steps of:

dispersing metal powder in an ultraviolet light-curable compound to prepare a flowable metal dispersion and separately, drawing a glass tube into a glass wire while heating the glass tube;

loading the flowable metal dispersion into the drawn glass wire;

exposing the flowable metal dispersion-loaded, drawn glass wire to ultraviolet light to cure the ultraviolet-curable compound in the flowable metal dispersion, thus forming at least one glass-coated metal microwire;

positioning the at least one glass-coated metal microwire in at least one of a plurality of grooves arranged in a width direction on a wire holder; and cutting the at least one glass-coated metal microwire positioned on the wire holder, in a traverse direction at predetermined distance gaps in a non-contact machining process using a laser having a pulse width shorter than the heat propagation time of the at least one glass-coated metal microwire to produce non-spherical/asymmetric fine particles, wherein the total diameter of the at least one glass-coated metal microwire ranges from 50 to 200 μm, and wherein the aspect ratio of nonspherical/asymmetric fine particles ranges from 2 to 15.

4. The method of claim 1, wherein the metal is in a form of metal powder having a diameter of 40 to 300 μm.

5. The method as in one of claims 1 to 3, wherein the metal or metal powder is (i) a magnetic metal or an alloy thereof, (ii) a magnetic metal or an alloy thereof plus copper (Cu), gold (Au), silver (Ag), iron (Fe), platinum (Pt), or a combination thereof, or (iii) copper (Cu), gold (Au), silver (Ag), iron (Fe), platinum (Pt), or a combination thereof.

6. The method of claim 5, wherein the magnetic metal is represented by the following General Formula 1:

    [General Formula 1]

wherein, TL is transition metal selected from the group consisting of Fe, Co, Ni and a combination thereof, TE is selected from the group consisting of Cr, Mo, Nb and a combination thereof, R is rare-earth metal selected from the group consisting of Gd, Tb, Sm and a combination thereof, M is selected from the group consisting of B, Si, C and a combination thereof, and x is 0.5 to 0.95.

7. The method of one of claims 1 to 3, wherein the glass is soda lime; borosilicate; aluminosilicate; silica; alkali silicate; Pyrex; quartz; or glass containing, as main ingredient, lead oxide, tellurium dioxide or silica.

8. The method as in either claim 1 or 2, wherein the cooling is conducted such that a coolant is sprayed to the surface of the wire in a direction traversing across the drawing direction.

9. The method as in either claim 1 or 2, wherein the glass-coated metal microwire has a metal core ranging in diameter from 30 to 100 μm and a glass coat layer ranging in thickness from 10 to 100 μm.

10. The method of claim 3, wherein the drawn glass wire has an inner diameter of 50 to 200 μm and a thickness of 100 to 500 μm.

11. The method of claim 3, wherein the ultraviolet light-curable compound is in a liquid phase of a monomer, an oligomer, a polymer, or a mixture thereof.

12. The method of claim 11, wherein the ultraviolet light-curable compound is a polyfunctional compound having a (meth)acrylate functional group.

13. The method of claim 11, wherein the ultraviolet light-curable compound is polyethylene glycol acrylate, polyethylene glycol diacrylate, polyethylene glycol methacrylate, acrylic acid, 2-hydroxyethyl methacrylate, 2-hydroxyethyl acrylate, 2-(2-ethoxyethoxy)enyl acrylate, tetrahydrofurfuryl acrylate, or a combination thereof.

14. The method of claim 13, wherein polyethylene glycol diacrylate has a number average molecular weight (Mn) of 100 to 1000.

15. The method of claim 11, wherein the flowable metal dispersion contains the metal powder in an amount of 50 to 90% by weight.

16. The method of claim 11, wherein the ultraviolet light is irradiated in a predetermined pattern to form codes corresponding to the ultraviolet irradiation pattern on a core region of the glass-coated metal microwire.

17. The method as in one of claims 1 to 3, wherein the laser is an infrared laser, near-infrared laser diode (DPSS) laser, or a femto-second (fs) laser.

18. The method of claim 17, wherein the laser is a pulse-type layer having a wavelength of 300 to 1,200 nm, with a pulse width of 290 fs or less.

19. A method for preparation of bioassay fine particles, comprising a step of immobilizing or binding a functional ingredient to a surface of the non-spherical/asymmetric fine particles produced according to one of claims 1 to 3, the functional ingredient being selected from the group consisting of functional groups of disease labeling materials, streptavidin, protein A, protein G, antibodies for immunoassay reagent, other ligand-specific molecules, and a combination thereof.

20. A method for preparation of security or identification fine particles, comprising a step of indexing or coding the surface of the non-spherical/asymmetric fine particles produced according to one of claims 1 to 3.

21. The method of claim 20, further comprising a step of incorporating the security or identification fine particles to a surface or to an inside of a substrate selected from the group consisting of paper, paperboards, foil, paper laminates, plastics, polymers, and fibers.

* * * * *